US007939647B2

(12) United States Patent
Kikawada et al.

(10) Patent No.: US 7,939,647 B2
(45) Date of Patent: May 10, 2011

(54) INSECT DESICCATION RESISTANCE GENES AND USES THEREOF

(75) Inventors: Takahiro Kikawada, Tsukuba (JP);
Takashi Okuda, Tsukuba (JP);
Masahiko Watanabe, Tsukuba (JP);
Kazuei Mita, Tsukuba (JP); Keiko Kadono, Tsukuba (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 0 days.

(21) Appl. No.: 12/313,645

(22) Filed: Nov. 21, 2008

(65) Prior Publication Data

US 2009/0124004 A1 May 14, 2009

Related U.S. Application Data

(62) Division of application No. 11/222,641, filed on Sep. 8, 2005, now Pat. No. 7,473,769.

(30) Foreign Application Priority Data

Sep. 8, 2004 (JP) ................................ 2004-261412

(51) Int. Cl.
*C12N 15/00* (2006.01)
*C12N 5/00* (2006.01)
*A61K 38/00* (2006.01)
(52) U.S. Cl. .................... 536/23.1; 435/320.1; 435/69.1; 435/325; 435/440
(58) Field of Classification Search ........................ None
See application file for complete search history.

(56) References Cited

U.S. PATENT DOCUMENTS

| 4,554,101 | A | 11/1985 | Hopp | |
|---|---|---|---|---|
| 5,858,712 | A * | 1/1999 | Hillman et al. | 435/69.1 |
| 6,291,438 | B1 | 9/2001 | Wang | |
| 6,562,958 | B1 * | 5/2003 | Breton et al. | 536/23.7 |
| 7,473,769 | B2 | 1/2009 | Kikawada et al. | |
| 7,557,201 | B2 * | 7/2009 | Fincher et al. | 536/23.6 |
| 7,572,902 | B2 * | 8/2009 | Abad et al. | 536/23.6 |

FOREIGN PATENT DOCUMENTS

WO WO0171042 A2 9/2001

OTHER PUBLICATIONS

Zhang et al. (1996) An analysis of base frequencies in the anti-sense strands corresponding to the 180 human protein coding sequences, Amino acids, vol. 10, pp. 253-262.*
Han et al. (1997) Changes in late-embryogenesis-abundant (LEA) messenger RNAs and dehydrins during maturation and premature drying of *Ricinus communis* L. seeds, PLanta, vol. 201, pp. 27-35.*
Thomson et al. (1998) the dhnA gene of *Escherichia coli* encodes a class I fructose bisphosphate aldolase, Biochem. J., vol. 331, Pt.2, pp. 437-445.*

Wise, Michael J., "LEAping to conclusions: A computational reanalysis of late embryogenesis abundant proteins and their possible roles", *BMC Bioinformatics*, vol. 4, No. 52, BioMed Central, pp. 1-19, Oct. 29, 2003 (Received May 29, 2003).
Belyavsky, A., et al., "PCR-based cDNA library construction: general cDNA libraries at the level of a few cells", *Nucleic Acids Research*, vol. 17, No. 8, IRL Press, pp. 2919-2932, Mar. 1989 (Received Feb. 14, 1989).
Frohman, Michael A., et al., "Rapid production of full-length cDNAs from rare transcripts: Amplification using a single gene-specific oligonucleotide primer", *Proc. Natl. Acad. Sci. USA*, vol. 85, Biochemistry, pp. 8998-9002, Dec., 1988 (Communicated Sep. 9, 1988).
Chomczynski, Piotr, et al., "Single-Step Method of RNA Isolation by Acid Guanidinium Thioyanate-Phenol-Chloroform Extraction",*Analytical Biochemistry*, vol. 162, Academic Press, Inc., pp. 156-159, 1987 (Received May 27, 1986).
Chirgwin, John M. et al "Isolation of Biologically Active Ribonucleic Acid from Sources Enriched in Ribonuclease", *Biochemistry*, American Chemical Society, pp. 5294-5299, 1979.
Kyte, Jack. et al, "A Simple Method for Displaying the Hydropathic Character of a Protein", *J. Mol. Biol.*, vol. 157, Academic Press Inc. (London) Ltd., pp. 105-132, 1982.
Altschul, Stephen F., et al, "Basic Local Alignment Search Tool", *J. Mol. Biol.*, vol. 215, Academic Press Limited, pp. 403-410, 1990.
Karlin, Samuel, et al. "Applications and statistics for multiple high-scoring segments in molecular sequences", *Proc. Natl. Acad. Sci.*, vol. 90, Evolution, pp. 5873-5877, Jun. 1993 (Contributed Mar. 24, 1993).
Browne, J., et al., "Plant Desiccation Gene Found in a Nematode," Nature, 416:38, (2002).
Dure, L. III, et al., "Developmental Biochemistry of Cottonseed Embryogenesis and Germination: Changing Messenger Ribonucleic Acid Populations As Shown by in Vitro and in Vivo Protein Synthesis," Biochemistry, 20:4162-4168, (1981).
Dure, L. III, "Structural Motifs in Lea Proteins," Plant Responses to Cellular Dehydration During Environmental Stress (Close, T.J. and Bray E.A., eds.). The American Society of Plant Physiologists, pp. 91-103, (1993).

(Continued)

Primary Examiner — Anand U Desai
Assistant Examiner — Samuel Liu
(74) Attorney, Agent, or Firm — Hamilton, Brook, Smith & Reynolds, P.C.

(57) ABSTRACT

An objective of the present invention is to provide polynucleotides encoding insect desiccation resistance proteins, and uses thereof. cDNA libraries were produced from *Polypedilum vanderplanki* larvae in a desiccated state, a *P. vanderplanki* EST database was constructed, and genes encoding LEA proteins were isolated. This resulted in the successful isolation of three types of novel gene encoding LEA-like proteins. When secondary structure predictions and motif searches were performed on the proteins deduced from each of the genes, all three proteins had α-helix-rich structures and LEA_4 motifs, which are characteristic of LEA proteins. Moreover, the recombinant proteins synthesized from these genes were heat soluble even when boiling, so that these proteins have hydrophilic properties as high as plant LEA proteins. Therefore, the three isolated genes were found to be novel *P. vanderplanki*-derived LEA genes. Furthermore, introduction of these genes into animal cells successfully conferred desiccation resistance to the cells.

8 Claims, 6 Drawing Sheets

OTHER PUBLICATIONS

Goyal, K., et al., "Transition from Natively Unfolded to Folded State Induced by Desiccation in an Anhydrobiotic Nematode Protein," J. Biol. Chem., 278(15):12977-12984, (2003).

Grzelczak, Z., et al., "Synthesis and Turnover of Proteins and mRNA in Germinating Wheat Embryos," Can. J. Biochem, 60(3):389-397, (1982).

Hinton, H.E., "Cryptobiosis in the Larva of Polypedilum Vanderplanki Hint. (Chirononmidae)," J. Ins. Physiol., 5:286-300, (1960).

Hinton, H.E., "A Fly Larva that Tolerates Dehydration and Temperatures of −270° to +102° C.," Nature, 188:336-337 (1960).

Ingram, J. and Bartels, D., "The Molecular Basis of Dehydration Tolerance in Plants," Annu. Rev. Plant Physiol. Plant Mol. Biol., 47:377-403, (1996).

Ma, X., et al., "A Small Stress Protein Acts Synergistically with Trehalose to Confer Desiccation Tolerance on Mammalian Cells," Cryobiology, 51(1):15-28, (2005).

Watanabe, M., et al., "Mechanism Allowing an Insect to Survive Complete Dehydration and Extreme Temperatures," J. Exp. Biol., 205:2799-2802, (2002).

Watanabe, M., et al., "Increase of Internal Ion Concentration Triggers Trehalose Synthesis Associated With Cryptobiosis in Larvae of Polypedilum Vanderplanki," J. Exp. Biol., 206:2281-2286, (2003).

Wise, M.J., and Tunnacliffe, A., "POPP the Question: What Do LEA Proteins Do?" Trends Plant Sci., 9(1): 13-17, (2004).

Browne, J.A., et al., "Dehydration-Specific Induction of Hydrophilic Protein Genes in the Anhydrobiotic Nematode Aphelenchus avenae," Eukaryotic Cell, 3(4): 966-975 (2004).

Gal, T. Z., et al., "An LEA group 3 family member is involved in survival of *C. elegans* during exposure to stress," FEBS Letters 577:21-26 (2004).

Goyal, K., "Dehydration-regulated processing of late embryogensis abundant protein in a desiccation-tolerant nematode," FEBS Letters, 579: 4093-4098 (2005).

Han el al. Changes in late embryogenesis-abundant (LEA) messenger RNAs and dehydrins during maturation and premature drying of *Ricinus communis* L. seeds, Planta., vol. 201, No. 1, pp. 27-35, (1997).

Thomson et al., The *dhnA* gene of *Escherichia coil* encodes a class I fructose bisphosphate aldolase, Biochem. J., vol, 331 (part 2), pp. 437-445 (1998).

Selisko et al, An insect-specific toxin from *Centruroides noxius* Hoffmann cDNA, primary structure, three-dimensional model and electrostatic surface potentials in comparison with other toxin variants, Eur. J. Biochem., vol. 242, No. 2, pp. 235-242 (1996).

Lapinski, J. and Tunnacliffe, A., "Anhydrobiosis Without Trehalose in Bdelloid Rotifers," *FEBS Letters* 553:387-390 (2003).

Office Action, (Restriction Requirement), U.S. Appl. No. 11/222,641, mailed Jul. 10, 2007.

Office Action, U.S. Appl. No. 11/222,641, mailed, Sep. 11, 2007.

Final Office Action, U.S. Appl. No. 11/222,641, mailed May 28, 2008.

Notice of Allowance, U.S. Appl. No. 11/222,641, mailed Oct. 2, 2008.

* cited by examiner

FIG. 1

| | |
|---|---|
| Aphelenchus avenae | ---------------------------------------------MSSQQNQNRQG |
| Betula pendula | -----------MASSREPKEKRAEAAAKLAASDLEDVKREREYEEQAKMEREELSLQQQ |
| Glycine max | -----------MASKK--QEERAEAAAKVAAKELEQVNRERRDRDFGVVAEQQQQHHQE |
| Zea mays | ---------------------MASHQDKASYQAGETKARTERKTGQAVGATKDTAQHAK |
| Arabidopsis thaliana | MTNLLALCLVLSTLLAAEVWSPSPAMTTHNTAVASEGEVIVKDGHHVVVVEYDRDGKTNT |

| | |
|---|---|
| Aphelenchus avenae | EQQE-----------QGYMEAAKEKVVNAWESTKETLSSTAQAAAEKTAEFRDSAGETIR |
| Betula pendula | QEDRPGVIGSVLKAVHETYEHAKEAVVGKTEETAESTRESGENAAEKARKTKDSAAEKTR |
| Glycine max | DQQKRGVIGSMFKAVQDTYENAKEAVVGKKEATNNAYSNTEVIHDVNIQPDDVSATGEVR |
| Zea mays | DR-----------AADAAGHAAGKGQDAKEATKQKASDTGSYLGKKTDEAKHKAGETT- |
| Arabidopsis thaliana | RVSISPPSADQGEEKENEVEMGTSMFRNVKEKAKETASYLPHVGQGISQPVMTDEARDHH |

| | |
|---|---|
| Aphelenchus avenae | DLTG-----------------QAQEKGQEFKERAGEKAEETK--------------- |
| Betula pendula | ETKKCAAEKAKEYKDYTAEKARETTEKARETKDSAAEKARETKDSAAEKAKEYKDYTAEK |
| Glycine max | DIS--ATKTHDIYDSATDNNNNKTGSKVGEYADYASQKAKETKDATMEKAGEYTDY---- |
| Zea mays | --------------------EATKHKAGETTEAAKQKAGETTEAAK------------- |
| Arabidopsis thaliana | ATAG------EVICDAFGKCRQKIASVVGRAKDRTVDSVGETASDVREAAAHKAHD---- |

| | |
|---|---|
| Aphelenchus avenae | ----------------------------------QRAGEKMDETKQRAGEMRENAG |
| Betula pendula | TRETRESAKEKAKEAAEKAKETKDSALGKAEEYKDYAAEKAKEAKDKTVGKASEYKDYAA |
| Glycine max | -------------ASQKAKEAKKTTMEKGGEYKDYSAEKAKERKDATVNKMGEYKDYAA |
| Zea mays | --------------------QKAGETTETTKQKAGETTEAAR |
| Arabidopsis thaliana | ------------------VKETVTHAARDVEDTVADQAQYAKGRVTEKAHDPKEGVA |

| | |
|---|---|
| Aphelenchus avenae | QKMEEYKQQGKGKAEELRDTAAEKLHQAGEKVKGRD--------------------- |
| Betula pendula | EKAKETKDSALGKAEEYKDYTAEKEKEVKDKTVGKAGEYKDYAAEKAKETKDYTAEKTIE |
| Glycine max | EKAKEGKDATVNKMGEYKDYAAEKTKEGKDATVNKMGEYKDYTAEKAKE---------- |
| Zea mays | QKAADAMEAAKQKAAEAGQYAKDTAVSGKDKSGG--------------------- |
| Arabidopsis thaliana | HKAHDAKESVADKAHDAKESVAQKAHDAKEKVREKAHDVKETVAQKAHESKERAKDRVRE |

| | |
|---|---|
| Aphelenchus avenae | ---------------------------------------------------- |
| Betula pendula | GKDTTLSKLGELKESAADAARKAMGFLSGKKDE-----------VTQKTEETKEATKEKL |
| Glycine max | GKDTTLGKLGELKDTASDAAKRAVGYLSGKKEETKEMASETAEATANKAGEMKEATKKKT |
| Zea mays | ----------------------------------------------------VI |
| Arabidopsis thaliana | KAQELKETATHKSKNAWERVKNGAREFGSATAATLSPTKVASIVGLTGIAAAPGTSVWVT |

| | |
|---|---|
| Aphelenchus avenae | ---------------------------------------------------- |
| Betula pendula | SEAKEEARRKMEELKVRGEENKDDADRKDREDNKVNEADRGTAATANIFSSLPSVTEAIK |
| Glycine max | AETAEAAKNKAGEIKDRAAETAEAAKNKTAETAEVTKNKALEMKDAAKDRTAETTDAAKQ |
| Zea mays | QQATEQVKSAAAGRKDAVMSTLGMGGDNKQGDANTNTNTNTTKDSSTITRDH-------- |
| Arabidopsis thaliana | FVSSYVLASVLGRQQFGVVQSKLYPVYPKATSVGILVGLFGHVLSRRRKLLTDATENWQG |

| | |
|---|---|
| Aphelenchus avenae | ---------------------------------------------------- |
| Betula pendula | RKLTQPSDVVDETRAAREHGSTGRKE-----------AGKVVVDVEETRPGYIAAKLKE |
| Glycine max | KTAQAKENTKENVSGAGETARRKMEEPKLQGKEGYGGRGDKVVVKVEESRPGAIAETLKA |
| Zea mays | ---------------------------------------------------- |
| Arabidopsis thaliana | VNLLSSFPMIEANKSFVEPRATKAMFERMKAEKEEGRGGERTSEQELRRKLEQLSERLSK |

| | | SEQ ID NO |
|---|---|---|
| Aphelenchus avenae | ---------------------------- | 7 |
| Betula pendula | SDQMAGQTFNDPGRRDDEGGIRLDRQGKM-- | 8 |
| Glycine max | ADQIAGQTFNDVGRFDEEGVVNVERRKK--- | 9 |
| Zea mays | ---------------------------- | 10 |
| Arabidopsis thaliana | LNTYSSWLNILTLMSLTWHFVYLGQRLGAAC | 11 |

FIG. 2

```
[22.7% / 132 aa]
    INT/OPT. Score : <     26/    162 >

AavLEA1    1'                                         MSSQQNQNRQGEQQEQGY
                                                      ..........
PvLEA1   181'  VYIYTIIDTLRFKYENHPPVNLLYTTLNSQKGNYREEDECNYCDETKSKFKEVKDAAGEK

AavLEA1   19'  MEAAKEKVVNAWESTKETLSSTAQAAAEKTAEFRDSAGETIRDLTGQAQEKGQEFKERAG
               ±±.±±±±....±..±...........±...±...±..±........±±......±...
PvLEA1   241'  MENAKEKIIQVKEAAKDKIGHAVDVTTDKLGQAKDATAEKLVQAKDATAEKLGYAKDVTA

AavLEA1   79'  EKAEEETKQRAGEKMDETKQRAGEMRENAGQKMEEYKQQGKCKAEELRDTAAEKLHQAGEK
               ±±.........±......±..±...±......±...........±..±.±±.±±.±±
PvLEA1   301'  EKLGLAAEKTKETLVDAKDTIVEAKDTTKEKLGHAADVTADKLGHAKDVTADKLGQAAEK

AavLEA1  139'  VKGRD
               .±
PvLEA1   361'  TKETLVDAKDATKDKLVQAKDVTADKLGHAKDVTKDKLAQAADKTKETLVETKDKTADKL
```

```
[27.5% / 131 aa]
    INT/OPT. Score : <     33/    137 >

AavLEA1    1'  MSSQQNQNRQGEQQEQGYMEAAKEKVVNAWESTKETLSSTAQAAAEKTAEFRDSAGETIR
               ....±..±.±±±±.......±....±..±±±.........
PvLEA2     1'         MKHDKGIIEEAKEKIIDVKDAAK----EKVQNAAETVKKALTGNEHEMD

AavLEA1   61'  DLTGQAQEKGQEFKERAGEKAEEETKQRAGEKMDETKQRAGEMRENAGQKMEEYKQQGKGK
               .±..±.±±..±±.±±±..±.....±....±.±±±.±....±.±±±.±......±.±
PvLEA2    46'  EAKQTIKDKAYETKEAVKDKAHETKEAIKDKAYDAKETVKEKYENAKEKVKDAGDGIKDK

AavLEA1  121'  AEELRDTAAEKLHQAGEKVKGRD
               ....±.....±.±±±±.±
PvLEA2   106'  YDATKEAARDTYEDAKKKVKGTDEEWKPMETKEEYLKDKYYKNNFNPIAIFESIMQPESS
```

```
[24.4% / 86 aa]
    INT/OPT. Score : <     16/     94 >

AavLEA1    1'                                                          MSSQQ

PvLEA3   181'  KEGVRDASGRVQENLQDVTGKVQDKFNDVSGSIKDNXPNVAGRVQDKFNDVSGAIKDNLP

AavLEA1    6'  NQNRQGEQQEQGYMEAAKEKVVNAWESTKETLSSTAQAAAEKTAEFRDSAGETIRDLTGQ
               ..±...±...±.±....±.....±
PvLEA3   241'  DVAGRVKDNLSEVTGKVQDKFNDVSGSIKDNLPNVAGKVQEGYENIKNRAPETFHDAKNR

AavLEA1   66'  AQEKGQEFKERAGEKAEEETKQRAGEKMDETKQRAGEMRENAGQKMEEYKQQGKGKAEELR
               .......±.±.±±±...±......±...±.±±±.
PvLEA3   301'  LXDSYDXIKRRVGEKYYDVKDQAQGTFYDVKNKAGEKLQDVANEETCSEISKYSFGALML

AavLEA1  126'  DTAAEKLHQAGEKVKGRD

PvLEA3   361'  FLIGANIVSIVAHYRLIKAVEESNASKLRLSLCYYKFFIGFKLVFLAILGVSSLYSEEMF
```

FIG. 4
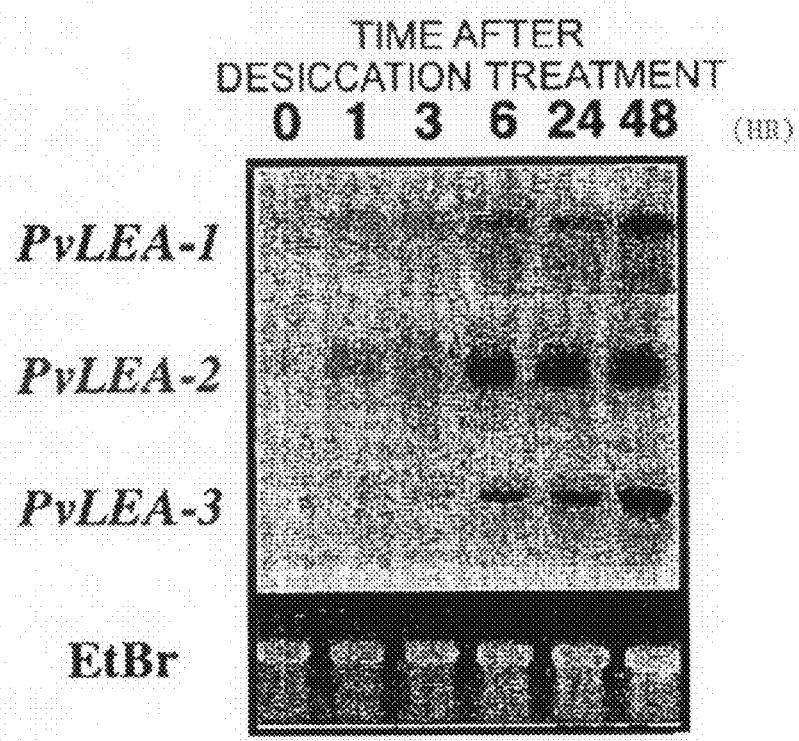
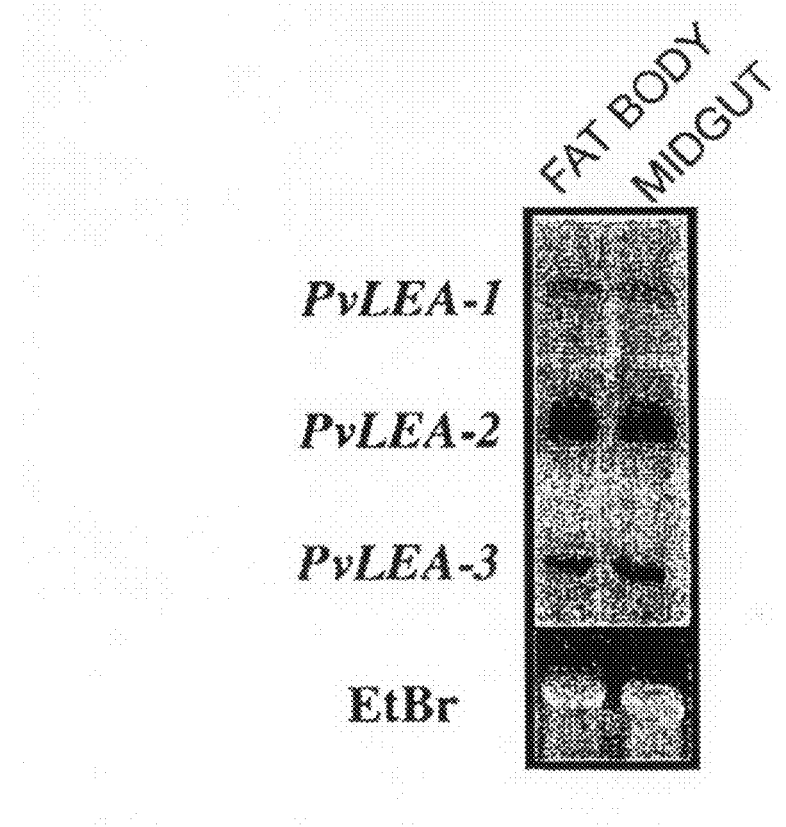

US 7,939,647 B2

INSECT DESICCATION RESISTANCE GENES AND USES THEREOF

RELATED APPLICATIONS

This application is a divisional of U.S. application Ser. No. 11/222,641, (now U.S. Pat. No. 7,473,769), filed Sep. 8, 2005, which claims priority under 35 U.S.C. §119 or 365 to Japanese Application No. 2004-261412, filed Sep. 8, 2004.

The entire teachings of the above applications are incorporated herein by reference.

FIELD OF THE INVENTION

The present invention relates to polynucleotides encoding insect-derived desiccation resistance proteins, and to uses thereof.

BACKGROUND OF THE INVENTION

*Polypedilum vanderplanki* only inhabits semi-arid regions of Africa, and is the only insect whose larvae can resume normal growth within one hour of being placed in water for absorption even after 48 hours of complete dehydration (Watanabe, M., Kikawada, T., Minagawa, N., Yukuhiro, F., and Okuda, T. (2002) J Exp Biol 205, 2799-2802). This state, in which the organism can recover even after complete desiccation, is called cryptobiosis. After entering a cryptobiotic state, *P. vanderplanki* can survive at temperatures from $-270°$ C. to $+102°$ C., or in 100% ethanol (Hinton, H. E. (1960) J Insect Phys 5, 286-300; and Hinton, H. E. (1960) Nature 188, 336-337). Trehalose has been said to be essential to inducing and maintaining the cryptobiotic state. However, even when desiccation occurs after accumulating a high concentration of trehalose in the body, there are some cases when the cryptobiotic state is not achieved (Watanabe, M., Kikawada, T., and Okuda, T. (2003) J Exp Biol 206, 2281-2286). Since trehalose accumulation alone is insufficient to explain the mechanism of cryptobiosis induction and maintenance, factors other than trehalose should be necessary for cryptobiosis.

The dormancy of plant seeds is a type of cryptobiosis. Seed dormancy occurs in late embryogenesis, and for approximately 20 years, proteins called late embryogenesis abundant (LEA) proteins have been known to accumulate specifically during this period (Dure, L., 3rd, Greenway, S. C., and Galau, G. A. (1981) Biochemistry 20, 4162-4168; Grzelczak, Z. F., Sattolo, M. H., Hanley-Bowdoin, L. K., Kennedy, T. D., and Lane, B. G (1982) Can J Biochem 60, 389-397). Under desiccation stimulus, expression of these proteins is increased not only in seeds, but also in pollen and in plant bodies (Ingram, J., and Bartels, D. (1996) Annu Rev Plant Physiol Plant Mol Biol 47, 377-403). LEA proteins have characteristic secondary structures and share an a-helix-rich structure (Goyal, K., Tisi, L., Basran, A., Browne, J., Burnell, A., Zurdo, J., and Tunnacliffe, A. (2003) J Biol Chem 278, 12977-12984). The results from transgenic yeast and rice have revealed that these proteins show stress-resistant functions such as desiccation resistance, cold resistance, and salinity resistance; however, the detailed biochemical functions (activities) of the proteins themselves are still unknown (Wise, M. J., and Tunnacliffe, A. (2004) Trends Plant Sci 9, 13-17). These proteins were thought to exist exclusively in plants. However, following their discovery in nematodes in 2002 (Browne, J., Tunnacliffe, A., and Burnell, A. (2002) Nature 416, 38), the existence of LEA proteins in organisms other than plants has been strongly suggested.

SUMMARY OF THE INVENTION

The present invention was made in view of such a situation, and an objective of the present invention is to provide polynucleotides encoding desiccation-resistance proteins of insects and uses thereof. More specifically, the present invention provides polynucleotides encoding *P. vanderplanki*-derived desiccation-resistance proteins, vectors carrying the polynucleotides, and uses thereof.

Since the LEA proteins of nematodes and plants are not highly homologous, RT-PCR and library screening are likely to be unavailable for isolating LEA genes of *P. vanderplanki*. Therefore, to solve the above-mentioned problems, the present inventors originally constructed EST database of *P. vanderplanki* using cDNA libraries from the larvae at 0, 12 and 36 hours after desiccation, so that they progressed isolation of genes for LEA proteins.

Thereby, the present inventors succeeded in isolating 3 types of novel genes (PvLEA1, PvLEA2, and PvLEA3) that encode LEA-like proteins. When secondary structure prediction and motif search were performed on the proteins deduced from the respective genes, these 3 proteins were found to have an α-helix-rich structure and LEA_4 motifs, which are characteristics of Group 3 LEA proteins. Consequently, the 3 genes isolated this time were suggested to be novel *P. vanderplanki*-derived LEA genes.

Next, when variations in expressions of the isolated LEA genes due to desiccation were investigated, the expression levels started to increase 1 hour after desiccation treatment, reached maximum values 6 hours after the treatment, and remained constant thereafter. Such behavior is similar to those reported so far for LEA genes, and therefore, PvLEA1, 2, and 3 genes were confirmed to be desiccation inducible.

Furthermore, the recombinant proteins synthesized from the three types of LEA genes isolated in the present invention were heat-treated, and the hydrophilicities of these proteins were examined. The results showed that the recombinant proteins do not aggregate at all, regardless of the heat treatment. This finding suggested that the translation products of the LEA genes of the present invention are highly hydrophilic proteins, exhibiting the activity of synonymous substitution for water; more specifically, it suggested that they function as desiccation resistance proteins.

Furthermore, cellular expression systems were used for examination to determine whether the LEA proteins of *P. vanderplanki* have desiccation-protective function in organisms. PvLEA1, 2, and 3 genes were introduced into CHO-K1 cells, and the number of cell colonies formed after desiccation treatment was determined. As a result, among cells that expressed the PvLEA1, 2, and 3 genes, only those cultured in a medium containing trehalose formed 33 to 55 colonies after desiccation treatment. On the other hand, cells that expressed only the vector formed hardly any colonies regardless of the presence of trehalose. Therefore, the coexistence of trehalose and expressed PvLEA1, 2, and 3 genes was found to confer desiccation resistance to animal cells.

To date, isolation of LEA genes from insects has never been reported, and the present invention provides the first example of isolating LEA genes from insects.

That is, the present invention relates to polynucleotides encoding the following insect-derived desiccation resistance proteins and uses thereof. More specifically, the present invention provides:

[1] an insect-derived polynucleotide of any one of (a) to (d),
  (a) a polynucleotide encoding a protein comprising the amino acid sequence of any one of SEQ ID NOs: 2, 4, and 6,
  (b) a polynucleotide comprising a coding region of the nucleotide sequence described in any one of SEQ ID NOs: 1, 3, and 5,
  (c) a polynucleotide encoding a protein comprising an amino acid sequence with one or more amino acid substitutions, deletions, additions, and/or insertions in the amino acid sequence of any one of SEQ ID NOs: 2, 4, and 6, and
  (d) a polynucleotide that hybridizes under stringent conditions with the polynucleotide comprising the nucleotide sequence of any one of SEQ ID NOs: 1, 3, and 5;

[2] the polynucleotide of [1], which is derived from *Polypedilum vanderplanki*;

[3] a vector comprising the polynucleotide of [1] or [2];

[4] a host cell carrying the polynucleotide of [1] or [2], or retaining the vector of [3];

[5] a pharmaceutical agent for conferring desiccation resistance to a cell, wherein the agent comprises the polynucleotide of [1] or [2], or the vector of [3];

[6] a method for conferring desiccation resistance to a cell, wherein the method comprises expressing in the cell a protein encoded by the polynucleotide of [1] or [2];

[7] a polynucleotide comprising the nucleotide sequence of any one of SEQ ID NOs: 1, 3, and 5, or comprising at least 15 nucleotides complementary to a complementary strand thereof;

[8] a method for determining whether a test cell has desiccation resistance, wherein the method comprises measuring the polynucleotide of [1] or an expression level of a protein encoded by the polynucleotide of [1] in the cell; and

[9] a method for determining a desiccation state of a test cell, wherein the method comprises measuring the polynucleotide of [1] or an expression level of a protein encoded by the polynucleotide of [1] in the cell.

BRIEF DESCRIPTION OF THE DRAWINGS

FIG. 1 compares the amino acid sequences of the desiccation-resistant nematode LEA (AavLEA1) and plant LEAs. The amino acid sequences of LEA proteins derived from a nematode (*Aphelenchus avenae*), European white birch (*Betula pendula*), soybean (*Glycine max*), corn (*Zea mays*), and *Arabidopsis thaliana* are shown in SEQ ID NOs: 7 to 11, respectively. Conserved regions could not be found on comparison of the LEA protein of the desiccation-resistant nematode with the LEA proteins of plants (*Betula pendula, Glycine max, Zea mays*, and *Arabidopsis thaliana*), FIG. 2 compares the amino acid sequences of *P. vanderplanki* LEA proteins (PvLEA1, set forth in SEQ ID NO:2, PvLEA2, set forth in SEQ ID NO:4, and PvLEA3 set forth in SEQ ID NO:6) and that of the nematode LEA protein (AavLEA1 set forth in SEQ ID NO:7). All three *P. vanderplanki* LEAs had low homology (30% or less) with AavLEA1.

FIG. 4 is a set of photographs showing variations in PvLEA gene expression after desiccation treatment. Expression levels of the three PvLEA genes began to increase one hour after desiccation treatment, reaching maximum values six hours after treatment, and remaining constant thereafter until individual larvae were completely desiccated, or more specifically, until they reached a cryptobiotic state. The PvLEA genes were not expressed tissue-specifically.

DETAILED DESCRIPTION OF THE INVENTION

Figure 3:
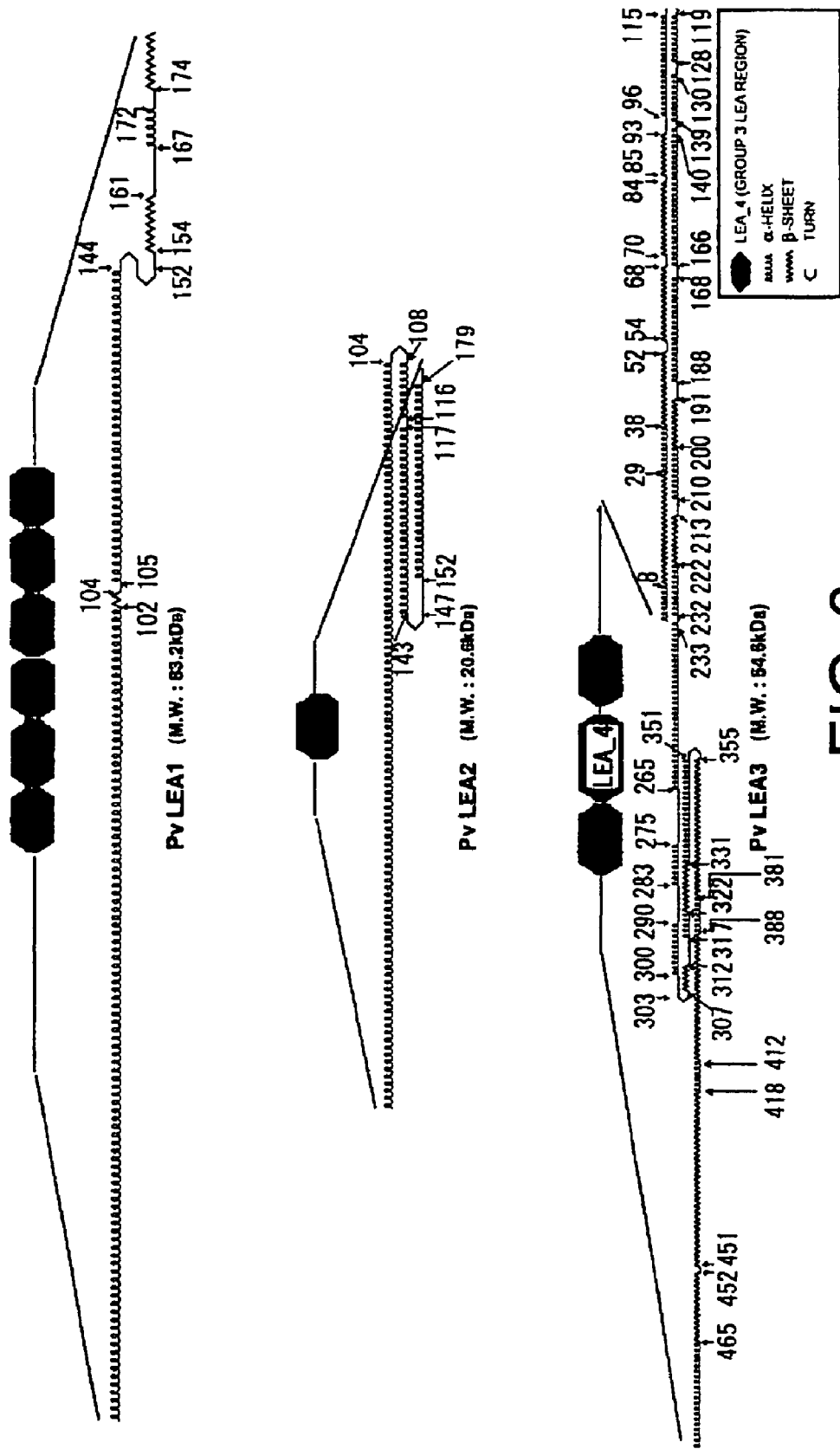
FIG. 3 shows the conserved domains of the PvLEA proteins and their secondary structures. A motif search using HMMER showed that the three PvLEA proteins comprised LEA_4 domains. Furthermore, the predicted secondary structures were rich in α-helix.

A description of example embodiments of the invention follows.

The present inventors succeeded in isolating three distinct genes encoding late embryogenesis abundant (LEA) proteins from *P. vanderplanki*. The present invention is based on these findings, and provides polynucleotides that encode the insect-derived LEA proteins and uses thereof. The nucleotide sequences of the genes encoding the three LEA proteins (PvLEA1, PvLEA2, and PvLEA3) derived from *P. vanderplanki* are shown in SEQ ID NOs: 1, 3, and 5, and the amino acid sequences of these proteins are shown in SEQ ID NOs: 2, 4, and 6, respectively.

The present invention provides insect-derived polynucleotides comprising a coding region of the nucleotide sequence of any one of SEQ ID NOs: 1, 3, and 5. The polynucleotides of the present invention comprise polynucleotides encoding proteins that are functionally equivalent to those comprising the amino acid sequence of SEQ ID NO: 2, 4, or 6. Such polynucleotides include polynucleotides encoding proteins comprising an amino acid sequence with one or more amino acid substitutions, deletions, additions, and/or insertions in the amino acid sequence of SEQ ID NO: 2, 4, or 6 (such as mutants, derivatives, alleles, variants, or homologs).

Herein, a "functionally equivalent protein" is a protein which makes cells desiccation resistant, and that has an a-helix-rich structure and at least one or more LEA_4 motifs, which are characteristic of LEA proteins. Proteins that do not aggregate after treatment with high temperature, and are highly hydrophilic can be included in the "functionally equivalent" proteins of the present invention. Whether a certain protein is functionally equivalent to the proteins of the present invention can be confirmed by predicting its secondary structure from the amino acid sequence of the test protein, and by conducting motif analysis. Alternatively, it can be judged by actually expressing the test protein in cells, and observing whether the cells become desiccation. Whether a certain protein is functionally equivalent to the proteins of the present invention can also be confirmed by expressing the test proteins, subjecting them to high temperature, and examining whether they are highly hydrophilic.

Proteins that are functionally equivalent to the insect-derived LEA proteins of the present invention can be prepared by those skilled in the art, for example, by using methods for introducing mutations to amino acid sequences in proteins (such as site-directed mutagenesis (Current Protocols in Molecular Biology edit. Ausubel et al. (1987) Publish. John Wiley & Sons Section 8.1-8.5)). Mutations in protein amino acid sequences due to mutations in the nucleotide sequences that encode the proteins may also occur in nature. Polynucleotides encoding such proteins that comprise an amino acid sequence with one or more amino acid substitutions, deletions, or additions to the naturally-occurring insect-derived LEA protein (SEQ ID NO: 2, 4, or 6) are comprised in the polynucleotides of the present invention, as long as they encode proteins functionally equivalent to the naturally occurring proteins. The number of modified amino acids is not particularly limited as long as the modified protein has functions equivalent to the LEA proteins of the present invention. However, the modified amino acids are generally 50 amino acids or less, preferably 30 amino acids or less, and more preferably 10 amino acids or less (for example, 5 amino acids or less, and 3 amino acids or less).

To retain the function of the protein, the amino acids used for substitution are preferably those comprising similar properties to the original amino acids prior to substitution. Examples of properties of amino acid side chains include: hydrophobic amino acids (A, I, L, M, F, P, W, Y, V), hydrophilic amino acids (R, D, N, C, E, Q, G, H, K, S, T), amino acids comprising the following side chains: aliphatic side-chains (G, A, V, L, I, P); hydroxyl group-containing side-chains (S, T, Y); sulfur atom-containing side-chains (C, M); carboxylic acid- and amide-containing side-chains (D, N, E, Q); base-containing side-chains (R, K, H); and aromatic-containing side-chains (H, F, Y, W) (The letters within parentheses indicate the one-letter amino acid codes).

The hydropathic index (Kyte and Doolitte, (1982) J Mol Biol. 1982 May 5; 157(1):105-32) or hydrophilicity value (U.S. Pat. No. 4,554,101) for each of the amino acids before and after modification is preferably within ±2, more preferably within ±1, and most preferably within ±0.5. The amino acid regions to be modified are not particularly limited, but regions other than those with characteristic motifs are preferred. Such regions other than those with characteristic motifs can be determined by referring to FIG. 3.

Proteins functionally equivalent to the insect-derived LEA proteins of the present invention can be isolated using hybridization techniques or gene amplification techniques well known to those skilled in the art. More specifically, using the nucleotide sequences of polynucleotides encoding the proteins of the present invention, or portions thereof, those skilled in the art can routinely perform hybridization (Current Protocols in Molecular Biology edit. Ausubel et al. (1987) Publisher: John Wiley & Sons Section 6.3-6.4) to isolate DNAs that are highly homologous to these nucleotide sequences, and to obtain functionally equivalent proteins from these DNAs. The present invention also comprises polynucleotides that hybridize under stringent conditions with the polynucleotides encoding the insect-derived LEA proteins of the present invention. The insects from which functionally equivalent proteins are isolated are preferably insects that are highly resistant to desiccation. Proteins that confer desiccation resistance to an organism may be present in such insects. Most preferably, such insects are *P. vanderplanki*, which are insects with the ability to recover from even complete desiccation (cryptobiosis).

Hybridization conditions for isolating DNAs encoding the functionally equivalent proteins can be appropriately selected by those skilled in the art. Conditions for hybridization may be stringent conditions. Herein, the phrase "stringent conditions" means conditions in which specific hybrids are formed, while non-specific hybrids are not formed. An embodiment of the stringent conditions of the present invention includes low stringency conditions. Low stringency conditions mean that the washing conditions after hybridization are, for example, 42° C., 5×SSPE, and 0.1% SDS, or preferably 50° C., 5×SSPE, and 0.1% SDS. Examples of hybridization conditions that are more preferable are highly stringent conditions. An example of highly stringent conditions is 65° C., 0.1× SSPE, and 0.1% SDS. Under such conditions, higher temperatures enable DNAs with higher homology to be obtained more efficiently. However, the combinations of SSPE, SDS, and temperature conditions mentioned above are only examples, and those skilled in the art can appropriately combine the above-mentioned or other factors (for example, probe concentration, probe length, and hybridization reaction time) that determine hybridization stringency to accomplish similar stringencies to those described above.

Alternatively, when using gene amplification techniques (PCR) (Current protocols in Molecular Biology edit. Ausubel et al. (1987) Publish. John Wiley & Sons Section 6.1-6.4), one can design primers based on portions of the nucleotide sequences of polynucleotides encoding the insect-derived LEA proteins of the present invention, then isolate polynucleotide fragments that are highly homologous to these nucleotide sequences or portions thereof, and obtain proteins that are functionally equivalent to the proteins of the present invention based on these fragments.

Proteins isolated using such hybridization techniques and gene amplification techniques ordinarily have amino acid sequences with high homology to the LEA proteins of the present invention. The present invention encompasses polynucleotides comprising nucleotide sequences with high homology to the nucleotide sequences of any one of SEQ ID NOs: 1, 3, and 5. Furthermore, the present invention encompasses proteins or peptides comprising amino acid sequences with high homology to the amino acid sequences of any one of SEQ ID NOs: 2, 4, and 6. "High homology" refers to sequence identity of at least 50% or more, preferably 75% or more, and more preferably 85% or more. More preferably, it means an identity of 90% or more, or 95% or more (such as 96% or more, 97% or more, 98% or more, or 99% or more). Identity can be determined using the BLAST algorithm.

The homologies of amino acid sequences and nucleotide sequences of the present invention can be determined using the BLAST algorithm according to Karlin and Altschul (Proc. Natl. Acad. Sci. USA 90:5873-5877, 1993). Programs called blastn and blastx have been developed based on this algorithm (Altschul et al., J. Mol. Biol. 215:403-410, 1990). When a nucleotide sequence is analyzed using blastn, based on BLAST, the parameters are set, for example, at score=100 and wordlength=12. Also, when an amino acid sequence is analyzed using blastx, based on BLAST, the parameters are set, for example, at score=50 and wordlength=3. When using the BLAST and Gapped BLAST programs, default parameters for each of the programs are used. Specific procedures for these analysis methods are known (www.ncbi.nlm.nih.gov/).

The polynucleotides of the present invention may be in any form as long as they encode the proteins of the present invention. More specifically, the polynucleotides may be cDNAs synthesized from mRNAs, genomic DNAs, chemically synthesized DNAs or such. Furthermore, polynucleotides with an arbitrary nucleotide sequence based on genetic code degeneracy are encompassed, as long as they encode the proteins of the present invention.

The polynucleotides of the present invention can be prepared by methods known to those skilled in the art. For example, cDNA libraries are constructed from insect larvae, and hybridization is conducted using DNA segments that encode insect-derived LEA proteins of the present invention as probes, thus preparing DNAs derived from nature. Furthermore, the polynucleotides of the present invention can be produced by preparing RNAs from insect larvae, synthesizing cDNAs using reverse transcriptase, synthesizing oligonucleotide DNAs based on the DNAs encoding the proteins of this invention, and then conducting PCR using the oligonucleotide DNAs as primers to amplify the cDNAs encoding the proteins of the present invention.

Known methods can be used to isolate mRNAs. For example, total RNA is prepared by guanidine ultracentrifugation (Chirgwin J. M. et al. Biochemistry 18:5294-5299 (1979)), AGPC methods (Chomczynski R and Sacchi N. Anal. Biochem. 162:156-159 (1987)), and so on, and mRNAs are purified from total RNA using mRNA Purification Kit (Amersham Biosciences) and such. Alternatively, mRNAs can be directly prepared using a QuickPrep mRNA Purification Kit (Amersham Biosciences).

The obtained mRNAs are used to synthesize cDNAs using reverse transcriptase. cDNAs can be synthesized using a kit such as SuperScript First-Strand Synthesis System for RT-PCR (Invitrogen). Alternatively, cDNAs can be synthesized and amplified by the 5'-RACE method (Frohman M. A. et al., Proc. Natl. Acad. Sci. U.S.A. 85: 8998-9002 (1988); Belyaysky A. et al., Nucleic Acids Res. 17: 2919-2932 (1989)) using 5'-Ampli FINDER RACE Kit (Clontech), and polymerase chain reaction (PCR).

The polynucleotides encoding the insect-derived LEA proteins of the present invention can be used to confer desiccation resistance to vertebrate cells, insect cells, or individual insects. More specifically, the present invention provides methods for conferring desiccation resistance to cells, in which the methods comprise expressing the insect-derived LEA proteins in the cells. Herein, the phrase "confer desiccation resistance (become desiccation resistant)" means that there is greater desiccation resistance than when an insect-derived LEA protein is not expressed. More preferably, this phrase means that expression of an insect-derived LEA protein enables acquisition of the ability to resuscitate after return to water, even when moisture was lost (cryptobiosis).

To express insect-derived LEA proteins in cells, the polynucleotides encoding the proteins must be introduced into cells. Genes are generally introduced into cells by incorporating the polynucleotides into appropriate vectors. The vectors that are used are not particularly limited, as long as the inserted polynucleotides are stably retained, and the vectors are selected appropriately according to the type of cells to be conferred with desiccation resistance. The present invention comprises vectors that comprise these polynucleotides that encode the insect-derived LEA proteins, and host cells that retain these vectors.

Host cells that express the insect-derived LEA proteins of the present invention include insect cells or vertebrate cells. Examples of insect cultured cells include Sf9 and Sf21 (both from Invitrogen), and examples of vertebrate cells include NIH/3T3, CHO, HepG2, and Jurkat. The vectors that enable genes to be expressed in these cells include the pIZT/V5-His vector (Invitrogen) for insect cultured cells. For vertebrate cells (in particular mammalian cells), the pGeneV5-His vector of the GeneSwitch system (Invitrogen) can be used for various cells such as NIH/3T3, CHO, HepG2, and Jurkat.

Vectors can be introduced into each of the host cells by appropriately using known gene introduction methods, according to the type of host cell. For methods involving transfection, methods such as calcium phosphate coprecipitation, electroporation, and complex formation with DEAE-dextran or with cationic lipids are used. For example, vectors are introduced into insect cultured cells using the cationic lipid for gene introduction, Cellfectin (Invitrogen®). Furthermore, for introduction of vectors into most vertebrate cells (in particular, mammalian cells), the cationic lipid for gene introduction, Lipofectamine2000 (Invitrogen®), can be used. For floating cells such as Jurkat cells, the cationic lipid for gene introduction reagent, DMRIE-C (Invitrogen®), may be used. When the insect-derived LEA proteins of the present invention are introduced and expressed in cells, trehalose may be added.

The polynucleotides encoding the insect-derived LEA proteins of the present invention, which can be utilized to confer desiccation resistance to vertebrate cells, insect cells, or individual insects, may be used in the form of pharmaceutical agents. More specifically, the present invention provides pharmaceutical agents for conferring desiccation resistance to cells, which comprise polynucleotides encoding the insect-derived LEA proteins, or vectors carrying these polynucleotides. In addition to the above-mentioned polynucleotides and vectors, the pharmaceutical agents of the present invention may appropriately comprise buffers such as TE buffer (10 mM Tris-Cl pH7.5, 1 mM EDTA), preservative solutions, or trehalose.

The present invention also provides oligonucleotides comprising at least 15 nucleotides that are complementary to the DNAs of the present invention, or to complementary strands thereof.

Herein, the term "complementary strand" refers to one strand of a double-stranded nucleic acid comprising A:T (U for RNA) and G:C base pairings to the other strand. In addition, "complementary" is defined as not only completely complementary within a continuous region of at least 15 nucleotides, but also having a homology of at least 70%, preferably at least 80%, more preferably 90%, and even more preferably 95% or more (for example, 96%, 97%, 98%, 99%, or higher) in a nucleotide sequence. Homology may be determined using an algorithm described herein. Furthermore, the term "oligonucleotide" includes polynucleotides.

The oligonucleotides of the present invention can be used as probes or primers for detecting and amplifying DNAs encoding the proteins of the present invention, and for detecting the expression of these DNAs. Furthermore, the oligonucleotides of the present invention can be used in the form of a DNA array platform.

When such oligonucleotides are used as primers, their lengths are normally 15 bp to 100 bp, and preferably 17 bp to 30 bp. The primers are not particularly limited as long as at least a portion of the DNAs of the present invention, or complementary strands thereof can be amplified. Furthermore, when using such oligonucleotides as primers, their 3' end regions can be designed to be complementary, and restriction enzyme recognition sequences or tags can be added to their 5' ends.

When using these oligonucleotides as probes, the probes are not particularly limited, as long as they specifically hybridize to at least a portion of the DNAs of the present invention, or complementary strands thereof. The probes may be synthetic oligonucleotides, and are normally at least 15 bp or longer.

When the oligonucleotides of the present invention are used as probes, they are preferably labeled as necessary. Examples of labeling methods include methods that use T4 polynucleotide kinase to phosphorylate the 5' ends of oligonucleotides with $^{32}P$, and methods that incorporate a substrate nucleotide, labeled with an isotope such as $^{32}P$, a fluorescent dye, or biotin, using a DNA polymerase such as Klenow enzyme, and using a random hexamer oligonucleotide or such as a primer (random priming methods and so on).

The oligonucleotides of the present invention can be produced using, for example, a commercially available oligonucleotide synthesizer. The probes may be produced as double-stranded DNA fragments obtained by restriction enzyme treatment.

The polynucleotides or the oligonucleotides of the present invention can be used to confirm whether the LEA proteins of the present invention are expressed in test cells. Furthermore, since the LEA proteins of the present invention are specifically expressed only in cells with desiccation resistance, the expression of the LEA proteins in these cells can be confirmed using the polynucleotides or oligonucleotides of the present invention to determine whether the test cells show desiccation resistance. Therefore, when the expressions of the LEA proteins are confirmed, the test cells can be determined to have desiccation resistance, and when the expressions of the LEA proteins are not confirmed, the test cells can be determined to have no desiccation resistance.

Furthermore, since the expression levels of the LEA proteins of the present invention increase as cell desiccation progresses, the expression levels of the LEA proteins can be examined to determine whether the test cells are in a desiccated state, or to confirm the degree of test cell desiccation. Therefore, when the expression levels of the LEA proteins are high, the desiccation state in the test cells can be determined to be progressing, and when the expression levels of the LEA proteins are low, the desiccation state in the test cells can be determined not to be progressing.

Methods well known to those skilled in the art may be used for quantifying the expression levels of the LEA proteins in the test cells. For example, the transcriptional levels of the LEA genes can be measured by extracting test cell mRNAs according to standard methods, and using these mRNAs as templates to perform Northern hybridization or RT-PCR. Furthermore, the expression levels of the LEA proteins can be measured using DNA array technology.

The translational levels of the genes can also be measured by detecting the expressions of the LEA proteins by electrophoresis, such as by SDS-PAGE.

Alternatively, as described in Example 2, the expressions of the LEA proteins can be confirmed by producing $^{32}P$ radiolabeled probes from full length LEA cDNAs using the Strip-EZ Kit (Ambion), and hybridizing the probes to a nylon membrane to which the RNAs of the test cells have been transferred.

Furthermore, the translational levels of the genes can be measured by performing Western blotting using antibodies against the LEA proteins, and detecting the expressions of the LEA proteins. The antibodies used for detecting the LEA proteins are not particularly limited, as long as they are detectable antibodies. However, for example, either monoclonal antibodies or polyclonal antibodies, or both may be used. The antibodies can be prepared by methods well known to those skilled in the art. For example, the polyclonal antibodies can be obtained as follows: An LEA protein or a recombinant protein expressed in a microorganism such as *E. coli* as a fusion protein with GST, or a partial peptide thereof, is used to immunize small animals such as rabbits to obtain their serums. The antibodies are prepared by purifying this serum using methods such as ammonium sulfate precipitation, protein A or protein G column chromatography, DEAE ion exchange chromatography, or chromatography through an affinity column coupled to the LEA protein or to a synthetic peptide. For monoclonal antibodies, for example, the LEA protein or a partial peptide thereof is used to immunize small animals such as mice, the spleens are removed from these mice and ground to separate the cells. These cells are fused to murine myeloma cells using reagents such as polyethylene glycol, and from the fused cells (hybridomas) thus obtained, clones that produce antibodies binding to the LEA protein are selected. Next, the obtained hybridomas are implanted intraperitoneally to mice, and their ascites are collected and purified by methods such as ammonium sulfate precipitation, protein A or protein G column chromatography, DEAE ion exchange chromatography, or chromatography through an affinity column coupled to the LEA protein or to a synthetic peptide to prepare monoclonal antibodies.

Expression of LEA proteins encoded by the genes of the present invention (PvLEA1, PvLEA2, and PvLEA3) that were isolated from *P. vanderplanki* is considered to enable organisms whose cells have been desiccated to recover from their desiccated state. Therefore, whether test cells have desiccation resistance can be determined by measuring the polynucleotides of the present invention or the expressions of the proteins encoded by these polynucleotides in these cells.

Furthermore, since the expression levels of the LEA proteins of the present invention increase as cell desiccation progresses, the polynucleotides of the present invention or the expression levels of the proteins encoded by these polynucleotides in test cells can be examined to determine whether the test cells are in a desiccated state, or to confirm the degree of test cell desiccation. In addition, expression of these genes in organisms other than *P. vanderplanki* enables these organisms (or tissues or cells) to be desiccated and preserved. For example, introduction of PvLEA1, PvLEA2, and PvLEA3 genes to natural enemy insects used in agriculture to eliminate insect pests, beneficial insects such as silkworms and honeybees, and laboratory insects such as fruit flies, allows preservation of lineages in the desiccated state without successive breeding. Furthermore, if insects to which these genes have been introduced are transported in a cryptobiotic state, insect death due to accidents during transport (damages due to warming, low temperature, and such) can be prevented, and the cost of transportation can be reduced due to reductions in weight. In addition, introducing these genes into vertebrates, if possible, will clearly contribute to desiccation and preservation technologies for these cells.

Therefore, the genes of the present invention (PvLEA1, PvLEA2, and PvLEA3) appear to be highly useful.

Any patents, published patent applications, and publications cited herein are incorporated by reference.

EXAMPLES

Hereinafter, the present invention will be specifically described using examples, however, it is not to be construed as being limited thereto.

Example 1

Isolation of *Polypedilum vanderplanki* Homologs of the LEA Genes

Since nematode and plant LEA proteins are not highly homologous (FIG. 1), the present inventors presumed that amino acid homologies between the LEA genes of *P. vanderplanki* and known LEA genes were also low, and that RT-PCR and library screening were unlikely to be effective in isolating the *P. vanderplanki* LEA genes. Therefore, the inventors prepared *P. vanderplanki* cDNA libraries 0, 12, and 36 hours after desiccation, constructed their own unique *P. vanderplanki* EST database, and then proceeded to isolate genes encoding LEA proteins with low homology.

ISOGEN (Nippon Gene) was used to extract total RNAs from *P. vanderplanki* larvae 0, 12, and 36 hours after desiccation. cDNAs were then synthesized using oligo dT primers, and these cDNAs were cloned into pBlueScript II KS+vectors (Stratagene) to produce cDNA libraries. Clones were randomly extracted from the three types of constructed libraries, and their nucleotide sequences were determined using T7 and T3 primers. An EST database was then constructed using the obtained data. As a result of BLAST searches (www.ncbi.nlm.nih.gov:80/BLAST) and annotations, clones that appeared to encode LEA proteins were identified. Clone contigs were constructed by aligning the identified clones, and the existence of the contigs thus-obtained was confirmed by RT-PCR. Finally, the full-length nucleotide sequences of the cDNAs were determined using the SMART-RACE method (Clontech).

As a result, three genes encoding distinct LEA-like proteins were successfully isolated, and they were named PvLEA1 (RNA: approximately 2500 nt, Protein: 742 AA), PvLEA2 (RNA: approximately 740 nt, Protein: 180 AA), and PvLEA3 (RNA: approximately 1560 nt, Protein: 484 AA). The nucleotide and amino acid sequences of PvLEA1 are shown in SEQ ID NOs: 1 and 2 respectively; the nucleotide and amino acid sequences of PvLEA2 are shown in SEQ ID NOs: 3 and 4 respectively; and the nucleotide and amino acid sequences of PvLEA3 are shown in SEQ ID NOs: 5 and 6 respectively.

The coding regions were identified from the obtained nucleotide sequence data using Genetyx-Mac (SDC), the amino acid sequences of the putative translation products were determined, and their secondary structures were then predicted. Further, motif analysis using HMMER (motif-.genome.adjp) was carried out to predict the function of these translation products. The results showed that these proteins all had low homology with the nematode LEA (AavLEA 1) protein: 24.6% for PvLEA1 protein, 28.0% for PvLEA2 protein, and 24.4% for PvLEA3 protein (FIG. 2).

Furthermore, according to Chou-Fasman secondary structure prediction, the proteins deduced from all three genes were predicted to have α-helix-rich structures, characteristic of LEA proteins. The results of motif searches using HMMER showed that all three isolated genes carried at least one or more LEA_4 motifs (FIG. 3). Therefore, the three genes isolated herein seemed to be novel insect-derived LEA genes.

Example 2

Expression Analysis of the LEA Genes

To investigate variations in the expression levels of the isolated LEA genes accompanying desiccation, total RNAs were extracted from *P. vanderplanki* larvae using ISOGEN (Nippon Gene) 0, 1, 3, 6, 24, and 48 hours after desiccation treatment. The obtained RNAs were subjected to electrophoresis using guanidine-denatured agarose gel, and were transferred to a nylon membrane using a vacuum blotter. Strip-EZ kit (Ambion) was used to produce $^{32}$P radiolabeled probes from the obtained full-length LEA cDNAs, and they were used in hybridization with the aforementioned nylon membrane. After washing so that only the specific bands remained, image analysis was performed using LAS-2500 (Fuji film). The results showed that the expression levels of the three isolated genes started to increase one hour after desiccation treatment, reached a maximum value six hours after treatment, and remained constant thereafter (FIG. 4). Therefore, PvLEA1, 2, and 3 genes are desiccation inducible. This finding is similar to the LEA genes reported so far.

Furthermore, to investigate the tissue specificity of LEA gene expression, the midguts were removed from larvae twelve hours after desiccation treatment, and tissues containing large amounts of fat body were separated. Image analysis of gene expression was carried out using RNA isolation, electrophoresis, and hybridization, as described above. Expression levels of PvLEA 1, 2 and 3 genes in the midgut were comparable to those in the tissue containing large amounts of fat body (FIG. 4). This therefore suggested that these genes are expressed and exert their functions in all tissues and cells.

Example 3

Study of the Hythophilicity of LEA Proteins

Since plant desiccation resistance proteins are highly hydrophilic, they are considered to have activities that allow synonymous substitution for water, and more specifically, they have been shown to function as ion scavengers and chaperonins (Dure, L., 3rd (1993) The American Society of Plant Physiologist Vol. 10, pp. 91-103; Ingram, J. and Bartels, D. (1996) Annu Rev Plant Physiol Plant Mol Biol 47, 377-403). Accordingly, if the LEA genes isolated in the present invention are similarly hydrophilic proteins, they may also have the functions proposed for hydrophilic proteins in plants. It is known that highly hydrophilic proteins do not aggregate when treated with boiling water (Dure, L., 3rd (1993) The American Society of Plant Physiologist Vol. 10, pp. 91-103).

Figure 5:
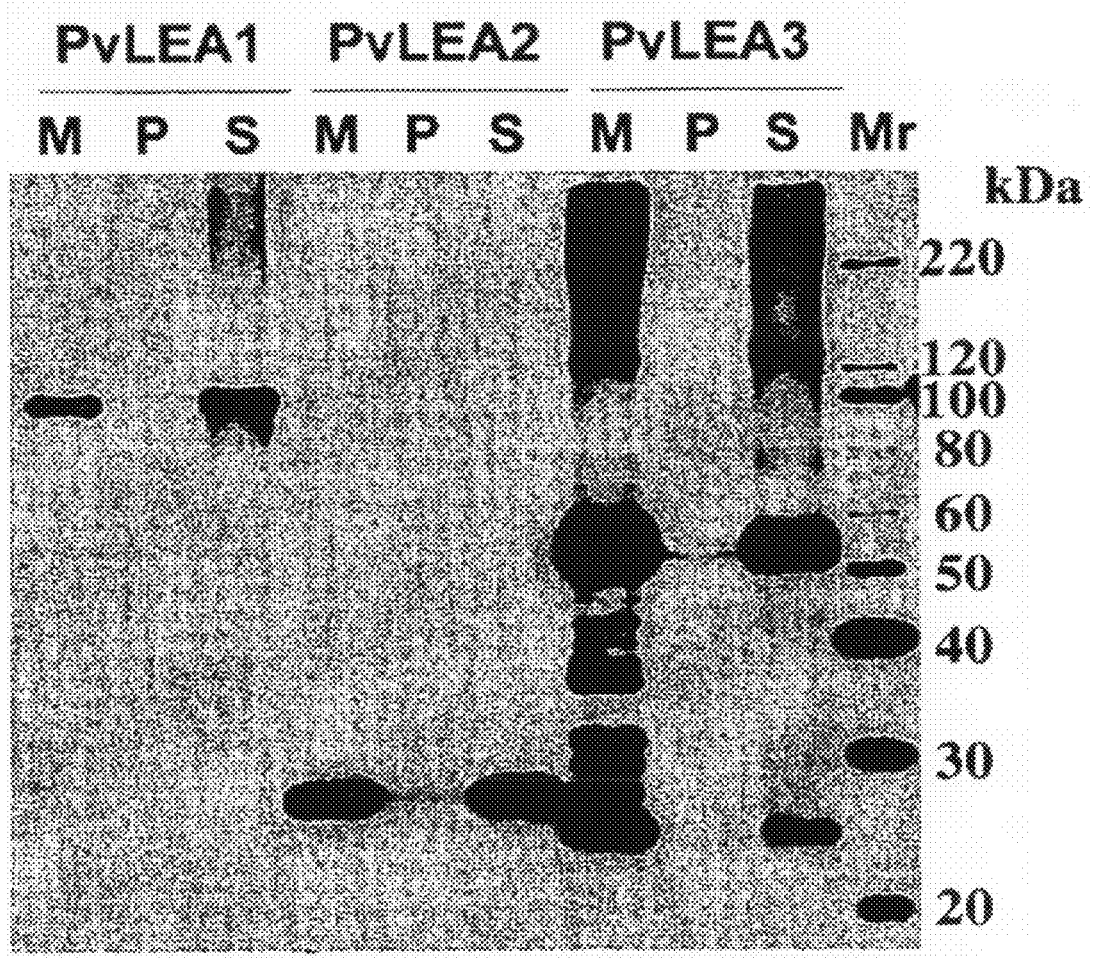
FIG. 5 is a photograph showing the results of studying the high hydrophilicity of the LEA proteins. PvLEA1, 2, and 3 proteins expressed using baculoviruses (M) were subjected to 100° C. for 15 minutes, and then fractionated into supernatant (S) and precipitate (P) by centrifugation. It should be noted that the molecular weights are increased by 2 kDa since the recombinant proteins are His-tagged (recombinant PvLEA1: about 100 kDa; recombinant PvLEA2: about 28 kDa; recombinant PvLEA3: about 55 kDa).
Figure 6:
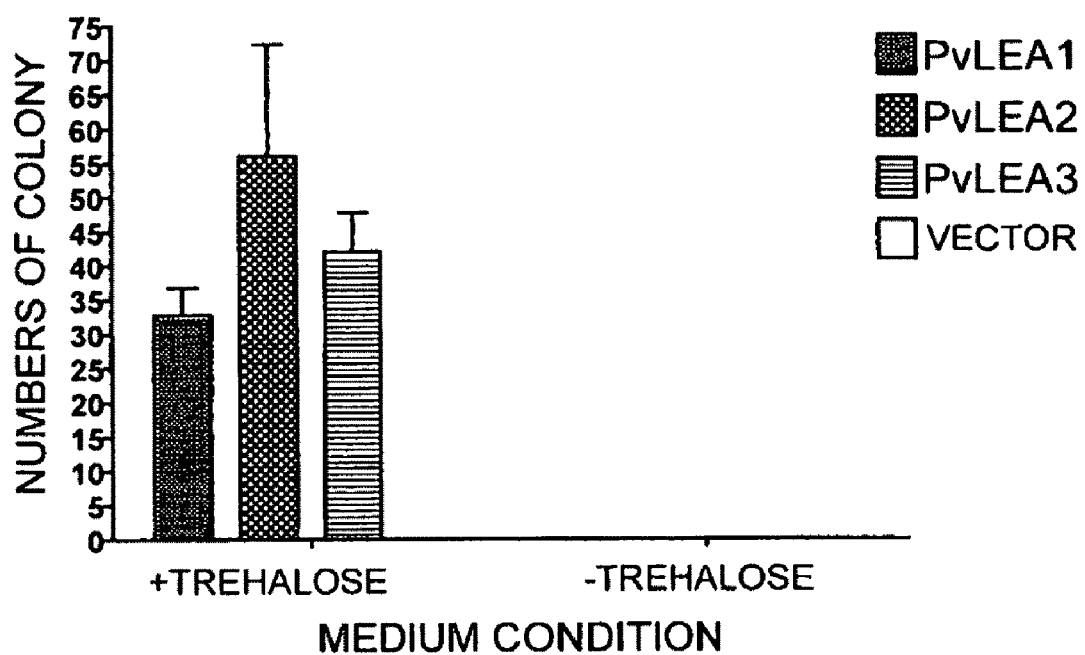
FIG. 6 shows the result of colony counting after introducing the PvLEA genes into CHO-K1 cells followed by desiccation treatment. Among the cells expressing the PvLEA1, 2, and 3 genes, only those cultured in the medium containing trehalose formed 30 to 55 colonies after desiccation treatment. On the other hand, cells that only expressed the vector hardly formed any colonies regardless of the presence of trehalose.

Thus, using the baculovirus protein expression system, recombinant His-tagged PvLEA1, PvLEA2, and PvLEA3 proteins were synthesized from LEA genes (M). These proteins were treated at 100° C. for 15 minutes, and then fractionated into supernatant (S) and precipitate (P) by centrifugation. Western blot analysis was performed on the obtained fractions using anti-His-tag antibody to determine whether or not the recombinant proteins were aggregated (FIG. 5). The results showed that the recombinant proteins synthesized from the three types of LEA genes isolated in the present invention did not aggregate at all, even though they were heat-treated. Therefore, the translation products of the LEA genes of the present invention were considered to be highly hydrophilic proteins, which have the activity of synonymous substitution for water, and more specifically, which function as desiccation resistance proteins.

Example 4

Desiccation-protective Function of Insect LEA Proteins

Next, cellular expression systems were used for examination to determine whether the LEA proteins of *P. vanderplanki* have desiccation-protective function in organisms.

The PvLEA1, 2, and 3 genes were respectively subcloned into the EcoRV/BamHI sites of pIRESneo3, pIRESbleo3, and pIRESpuro3 vectors (Clontech) to construct pPvLEA1-IRES-neo3, pPvLEA2-IRES-bleo3, and pPvLEA3-IRES-puro3 plasmids. These plasmids were introduced into 50% confluent CHO-KI cells (a cell line derived from Chinese hamster ovary cells) using FuGene6 (Roche), and the media were exchanged 24 hours later with either 0.1 M trehalose-containing medium-or trehalose-free medium. Cells to which the genes were introduced were cultured continuously for two days, followed by complete removal of the medium, and the cells were left to stand for 4 hours in a sealed container at a relative humidity of 95%. The cells were suspended in Ham's F-12 medium for rehydration, and plated on a 12-well culture plate ($5\times10^4$ cell/well). After culturing for six days, the number of cell colonies that formed was determined. The CHO-K1 cells were cultured in 10% fetal calf serum-containing Ham's F-12 medium (Sigma) at 95% humidity, 5% carbon dioxide and 37° C.

As a result of the above examination, among the cells expressing the PvLEA1, 2, and 3 genes, only those cultured in the medium containing trehalose formed 30 to 55 colonies after desiccation treatment. On the other hand, cells that expressed only the vector formed hardly any colonies regardless of the presence of trehalose. Therefore, the coexistence of trehalose and expressed PvLEA 1, 2, and 3 genes was found to confer desiccation resistance to animal cells.

What is claimed is:

1. An isolated insect-derived polynucleotide, the polynucleotide is selected from the group consisting of: (a) a polynucleotide encoding a protein comprising the amino acid sequence of SEQ ID NO:4; and (b) a polynucleotide comprising a coding region for encoding the amino acid sequence of SEQ ID NO:4 in the nucleotide sequence of SEQ ID NO:3.

2. The polynucleotide of claim 1, which is derived from *Polypedilum vanderplanki*.

3. A vector comprising the polynucleotide of claim 1.

4. A host cell transformed with polynucleotide of claim 1.

5. A host cell containing the vector of claim 3.

6. An agent for conferring desiccation resistance to a cell, wherein the agent comprises an isolated insect-derived polynucleotide of (a) or (b):

(a) a polynucleotide encoding a protein comprising the amino acid sequence of SEQ ID NO:4; or (b) a polynucleotide comprising a coding region for encoding the amino acid sequence of SEQ ID NO:4 in the nucleotide sequence of SEQ ID NO:3.

7. An agent for conferring desiccation resistance to a cell, wherein the agent comprises a vector comprising an isolated insect-derived polynucleotide of (a) or (b):

(a) a polynucleotide encoding a protein comprising the amino acid sequence of SEQ ID NO:4; or (b) a polynucleotide comprising a coding region for encoding the amino acid sequence of SEQ ID NO:4 in the nucleotide sequence of SEQ ID NO:3.

8. An isolated polynucleotide comprising the nucleotide sequence of SEQ ID NO:3.

* * * * *

SEQUENCE LISTING

```
<160> NUMBER OF SEQ ID NOS: 12

<210> SEQ ID NO 1
<211> LENGTH: 2531
<212> TYPE: DNA
<213> ORGANISM: Polypedilum vanderplanki
<220> FEATURE:
<221> NAME/KEY: CDS
<222> LOCATION: (21)..(2246)
<223> OTHER INFORMATION:

<400> SEQUENCE: 1
gttgaacaca cgtaacaatc atg gta cta gga agt att tta aga gtt gat act      53
                     Met Val Leu Gly Ser Ile Leu Arg Val Asp Thr
                       1               5                      10 tgt ctt tgc tgc ttt cgc att gag tca ggt gga ata ttt gtt gga gct       101
Cys Leu Cys Cys Phe Arg Ile Glu Ser Gly Gly Ile Phe Val Gly Ala
             15                  20                  25 ttc gga tta ttc tac gca gtt atc caa att ttt gct caa ata tgt tta       149
Phe Gly Leu Phe Tyr Ala Val Ile Gln Ile Phe Ala Gln Ile Cys Leu
         30                  35                  40 atg ata tat ttg atg gct gtc gaa aat ttc tgt cca gag cga ttt ttt       197
Met Ile Tyr Leu Met Ala Val Glu Asn Phe Cys Pro Glu Arg Phe Phe
     45                  50                  55 gca cat gat aat cga att gat aga caa ata cgt cat gat gta gca aat       245
Ala His Asp Asn Arg Ile Asp Arg Gln Ile Arg His Asp Val Ala Asn
 60                  65                  70                  75 gtt acc aat atg gct tta gaa aac atc caa aat gtc act aac act gat       293
Val Thr Asn Met Ala Leu Glu Asn Ile Gln Asn Val Thr Asn Thr Asp
                 80                  85                  90 ctc aca tgc act caa att aac aaa att ccc gtt ggt ctc ttg tta atc       341
Leu Thr Cys Thr Gln Ile Asn Lys Ile Pro Val Gly Leu Leu Leu Ile
             95                 100                 105 att gga ata att ttg aat tta att tca att att gcg cat tac aga ttg       389
Ile Gly Ile Ile Leu Asn Leu Ile Ser Ile Ile Ala His Tyr Arg Leu
        110                 115                 120 gtc aaa gga att gaa gaa tcc aat gtt cat aaa ttc ccc ttg aca ctt       437
Val Lys Gly Ile Glu Glu Ser Asn Val His Lys Phe Pro Leu Thr Leu
    125                 130                 135 aac tac tac aaa ttc tgg att gga att aaa tta att ctt ttg gcc att       485
Asn Tyr Tyr Lys Phe Trp Ile Gly Ile Lys Leu Ile Leu Leu Ala Ile
140                 145                 150                 155 ttt ggt gtt tgg act ttc ttc aat tct aaa atg att tgg att gca att       533
Phe Gly Val Trp Thr Phe Phe Asn Ser Lys Met Ile Trp Ile Ala Ile
                160                 165                 170 gtg act ttg ctc ctt ctc ttg ttc gat gtt tat att tac acc atc att       581
Val Thr Leu Leu Leu Leu Leu Phe Asp Val Tyr Ile Tyr Thr Ile Ile
            175                 180                 185 gat aca ctt cgt ttc aag tat gaa aat cac cca ccg gta aat ctt ctc       629
```

```
Asp Thr Leu Arg Phe Lys Tyr Glu Asn His Pro Pro Val Asn Leu Leu
        190                 195                 200 tat aca act ttg aat tca caa aag gga aat tat aga gaa gaa gat gaa          677
Tyr Thr Thr Leu Asn Ser Gln Lys Gly Asn Tyr Arg Glu Glu Asp Glu
205                 210                 215 tgc aat tac tgt gat gaa aca aaa agt aaa ttc aag gaa gtt aaa gat          725
Cys Asn Tyr Cys Asp Glu Thr Lys Ser Lys Phe Lys Glu Val Lys Asp
220                 225                 230                 235 gct gca ggt gaa aaa atg gaa aat gct aaa gaa aaa atc att caa gtc          773
Ala Ala Gly Glu Lys Met Glu Asn Ala Lys Glu Lys Ile Ile Gln Val
                240                 245                 250 aaa gaa gct gca aaa gat aaa att ggg cat gct gtt gat gtt aca aca          821
Lys Glu Ala Ala Lys Asp Lys Ile Gly His Ala Val Asp Val Thr Thr
            255                 260                 265 gat aag ctt ggt caa gcc aag gat gcc act gct gaa aaa tta gta caa          869
Asp Lys Leu Gly Gln Ala Lys Asp Ala Thr Ala Glu Lys Leu Val Gln
        270                 275                 280 gca aaa gat gca act gca gaa aag tta ggt tat gca aag gat gtc act          917
Ala Lys Asp Ala Thr Ala Glu Lys Leu Gly Tyr Ala Lys Asp Val Thr
285                 290                 295 gct gaa aaa ctt gga ctt gct gct gaa aaa act aaa gaa act tta gtt          965
Ala Glu Lys Leu Gly Leu Ala Ala Glu Lys Thr Lys Glu Thr Leu Val
300                 305                 310                 315 gat gct aaa gat acc att gtt gaa gca aag gat aca act aaa gaa aaa         1013
Asp Ala Lys Asp Thr Ile Val Glu Ala Lys Asp Thr Thr Lys Glu Lys
                320                 325                 330 ctc gga cat gct gct gat gtc aca gct gat aaa ctt ggt cat gca aag         1061
Leu Gly His Ala Ala Asp Val Thr Ala Asp Lys Leu Gly His Ala Lys
            335                 340                 345 gac gtc act gca gat aag tta ggt caa gca gca gaa aaa act aaa gaa         1109
Asp Val Thr Ala Asp Lys Leu Gly Gln Ala Ala Glu Lys Thr Lys Glu
        350                 355                 360 aca tta gtg gat gca aaa gat gca aca aag gat aaa ctt gtt caa gct         1157
Thr Leu Val Asp Ala Lys Asp Ala Thr Lys Asp Lys Leu Val Gln Ala
365                 370                 375 aag gac gta act gct gat aaa ctt ggt cat gct aaa gat gtt aca aaa         1205
Lys Asp Val Thr Ala Asp Lys Leu Gly His Ala Lys Asp Val Thr Lys
380                 385                 390                 395 gat aag ttg gct caa gct gct gac aag act aaa gag act ttg gtt gaa         1253
Asp Lys Leu Ala Gln Ala Ala Asp Lys Thr Lys Glu Thr Leu Val Glu
                400                 405                 410 aca aaa gac aaa aca gca gat aaa cta gga caa gct gca gat aag aca         1301
Thr Lys Asp Lys Thr Ala Asp Lys Leu Gly Gln Ala Ala Asp Lys Thr
            415                 420                 425 aaa gaa aaa ctt gtt gaa gct aaa gat gtg act gct gat aag cta gga         1349
Lys Glu Lys Leu Val Glu Ala Lys Asp Val Thr Ala Asp Lys Leu Gly
        430                 435                 440 cat gca aag gat gtc act gca gat aaa ctt gga aga gca gca gaa aaa         1397
His Ala Lys Asp Val Thr Ala Asp Lys Leu Gly Arg Ala Ala Glu Lys
445                 450                 455 aca aaa gaa act tta gtt gat gca aag gat aca aca aag gat aaa ctt         1445
Thr Lys Glu Thr Leu Val Asp Ala Lys Asp Thr Thr Lys Asp Lys Leu
460                 465                 470                 475 gct tat gct aag gat gtc act gct gat aaa ctt aat tat gct gca gac         1493
Ala Tyr Ala Lys Asp Val Thr Ala Asp Lys Leu Asn Tyr Ala Ala Asp
                480                 485                 490 aaa act aag gaa aaa ctt gtt gat gct aaa gat aca aca aaa gac aag         1541
Lys Thr Lys Glu Lys Leu Val Asp Ala Lys Asp Thr Thr Lys Asp Lys
            495                 500                 505 ctt gga tat gct gca gat aag aca aaa gaa aaa ctt gca gat gct aag         1589
```

```
                Leu Gly Tyr Ala Ala Asp Lys Thr Lys Glu Lys Leu Ala Asp Ala Lys
                    510                 515                 520 gat aca aca aag gat aaa ttt ggt gat gca aaa gaa gca aca aaa gac       1637
Asp Thr Thr Lys Asp Lys Phe Gly Asp Ala Lys Glu Ala Thr Lys Asp
        525                 530                 535 aaa tat gaa gat gct aaa caa aaa atg gct gaa aca aag gac aaa gct       1685
Lys Tyr Glu Asp Ala Lys Gln Lys Met Ala Glu Thr Lys Asp Lys Ala
540                 545                 550                 555 aaa gaa aag ttc ttt gaa gca aag gat gca act gct gat aaa ttg ggc       1733
Lys Glu Lys Phe Phe Glu Ala Lys Asp Ala Thr Ala Asp Lys Leu Gly
                560                 565                 570 aat gca aaa gat gca act aaa gat aaa ctt ggc tat gct gct gat aaa       1781
Asn Ala Lys Asp Ala Thr Lys Asp Lys Leu Gly Tyr Ala Ala Asp Lys
            575                 580                 585 act aaa gaa aag tat gat gaa gca aag gat gca aca aaa gat aag ctt       1829
Thr Lys Glu Lys Tyr Asp Glu Ala Lys Asp Ala Thr Lys Asp Lys Leu
        590                 595                 600 ggt tat gcc aag gat aaa cta gtc gaa act aaa gat gca gct aaa gat       1877
Gly Tyr Ala Lys Asp Lys Leu Val Glu Thr Lys Asp Ala Ala Lys Asp
    605                 610                 615 aag aca aag gaa aag tat gaa gaa gca aaa gac aaa ttt ggt caa gca       1925
Lys Thr Lys Glu Lys Tyr Glu Glu Ala Lys Asp Lys Phe Gly Gln Ala
620                 625                 630                 635 aga gat gta act aaa gaa aga tgg gat gaa aca aaa gat gca gcc aaa       1973
Arg Asp Val Thr Lys Glu Arg Trp Asp Glu Thr Lys Asp Ala Ala Lys
                640                 645                 650 aat aag tat ggt gac atg aga agc aat gtt caa atg gaa aat tgg aat       2021
Asn Lys Tyr Gly Asp Met Arg Ser Asn Val Gln Met Glu Asn Trp Asn
            655                 660                 665 aat acc aga gat aga tat gga aat gtg att caa aga cca gat gaa cca       2069
Asn Thr Arg Asp Arg Tyr Gly Asn Val Ile Gln Arg Pro Asp Glu Pro
        670                 675                 680 aga gac aaa att aca gtc gct gca gtc act aca aga gaa act gtc act       2117
Arg Asp Lys Ile Thr Val Ala Ala Val Thr Thr Arg Glu Thr Val Thr
    685                 690                 695 caa atc aga aag gat aat gaa cca caa aca atc atc aat gat aat cca       2165
Gln Ile Arg Lys Asp Asn Glu Pro Gln Thr Ile Ile Asn Asp Asn Pro
700                 705                 710                 715 caa aag gca aga tat ttt gag caa tat tca gca gtt tat gta aac cca       2213
Gln Lys Ala Arg Tyr Phe Glu Gln Tyr Ser Ala Val Tyr Val Asn Pro
                720                 725                 730 caa gat caa caa aaa atg gac aaa ata att tgc taaactttca taaatttgat    2266
Gln Asp Gln Gln Lys Met Asp Lys Ile Ile Cys
            735                 740 attcattctt aatttattac ttttctgctt gttcattttt aaagtataat taataaatat    2326
ttaagaaagt atttgtaagt cattaattgt ctatgtgtgc ttttcatatg tgcacaaata    2386
aaaatatcta attgtagctt atatttgcat gaattttgaa aaaaaaagat tactaaaatg    2446
tagaatttta ttggaatttc caatgatgaa ataaaagtat ttaatcaaaa taaaatttta    2506
atacccaaaa aaaaaaaaaa aaaaa                                          2531

<210> SEQ ID NO 2
<211> LENGTH: 742
<212> TYPE: PRT
<213> ORGANISM: Polypedilum vanderplanki

<400> SEQUENCE: 2

Met Val Leu Gly Ser Ile Leu Arg Val Asp Thr Cys Leu Cys Cys Phe
1               5                   10                  15
```

-continued

```
Arg Ile Glu Ser Gly Gly Ile Phe Val Gly Ala Phe Gly Leu Phe Tyr
             20                  25                  30
Ala Val Ile Gln Ile Phe Ala Gln Ile Cys Leu Met Ile Tyr Leu Met
         35                  40                  45
Ala Val Glu Asn Phe Cys Pro Glu Arg Phe Phe Ala His Asp Asn Arg
 50                  55                  60
Ile Asp Arg Gln Ile Arg His Asp Val Ala Asn Val Thr Asn Met Ala
 65                  70                  75                  80
Leu Glu Asn Ile Gln Asn Val Thr Asn Thr Asp Leu Thr Cys Thr Gln
                 85                  90                  95
Ile Asn Lys Ile Pro Val Gly Leu Leu Ile Ile Gly Ile Ile Leu
             100                 105                 110
Asn Leu Ile Ser Ile Ile Ala His Tyr Arg Leu Val Lys Gly Ile Glu
             115                 120                 125
Glu Ser Asn Val His Lys Phe Pro Leu Thr Leu Asn Tyr Tyr Lys Phe
     130                 135                 140
Trp Ile Gly Ile Lys Leu Ile Leu Leu Ala Ile Phe Gly Val Trp Thr
145                 150                 155                 160
Phe Phe Asn Ser Lys Met Ile Trp Ile Ala Ile Val Thr Leu Leu Leu
                 165                 170                 175
Leu Leu Phe Asp Val Tyr Ile Tyr Thr Ile Ile Asp Thr Leu Arg Phe
             180                 185                 190
Lys Tyr Glu Asn His Pro Pro Val Asn Leu Leu Tyr Thr Thr Leu Asn
         195                 200                 205
Ser Gln Lys Gly Asn Tyr Arg Glu Glu Asp Glu Cys Asn Tyr Cys Asp
 210                 215                 220
Glu Thr Lys Ser Lys Phe Lys Glu Val Lys Asp Ala Ala Gly Glu Lys
225                 230                 235                 240
Met Glu Asn Ala Lys Glu Lys Ile Ile Gln Val Lys Glu Ala Ala Lys
                 245                 250                 255
Asp Lys Ile Gly His Ala Val Asp Val Thr Thr Asp Lys Leu Gly Gln
             260                 265                 270
Ala Lys Asp Ala Thr Ala Glu Lys Leu Val Gln Ala Lys Asp Ala Thr
         275                 280                 285
Ala Glu Lys Leu Gly Tyr Ala Lys Asp Val Thr Ala Glu Lys Leu Gly
     290                 295                 300
Leu Ala Ala Glu Lys Thr Lys Glu Thr Leu Val Asp Ala Lys Asp Thr
305                 310                 315                 320
Ile Val Glu Ala Lys Asp Thr Thr Lys Glu Lys Leu Gly His Ala Ala
                 325                 330                 335
Asp Val Thr Ala Asp Lys Leu Gly His Ala Lys Asp Val Thr Ala Asp
             340                 345                 350
Lys Leu Gly Gln Ala Ala Glu Lys Thr Lys Glu Thr Leu Val Asp Ala
         355                 360                 365
Lys Asp Ala Thr Lys Asp Lys Leu Val Gln Ala Lys Asp Val Thr Ala
     370                 375                 380
Asp Lys Leu Gly His Ala Lys Asp Val Thr Lys Asp Lys Leu Ala Gln
385                 390                 395                 400
Ala Ala Asp Lys Thr Lys Glu Thr Leu Val Glu Thr Lys Asp Lys Thr
                 405                 410                 415
Ala Asp Lys Leu Gly Gln Ala Ala Asp Lys Thr Lys Glu Lys Leu Val
             420                 425                 430
Glu Ala Lys Asp Val Thr Ala Asp Lys Leu Gly His Ala Lys Asp Val
         435                 440                 445
```

```
Thr Ala Asp Lys Leu Gly Arg Ala Ala Glu Lys Thr Lys Glu Thr Leu
    450                 455                 460

Val Asp Ala Lys Asp Thr Thr Lys Asp Lys Leu Ala Tyr Ala Lys Asp
465                 470                 475                 480

Val Thr Ala Asp Lys Leu Asn Tyr Ala Ala Asp Lys Thr Lys Glu Lys
                485                 490                 495

Leu Val Asp Ala Lys Asp Thr Thr Lys Asp Lys Leu Gly Tyr Ala Ala
            500                 505                 510

Asp Lys Thr Lys Glu Lys Leu Ala Asp Ala Lys Asp Thr Thr Lys Asp
        515                 520                 525

Lys Phe Gly Asp Ala Lys Glu Ala Thr Lys Asp Lys Tyr Glu Asp Ala
    530                 535                 540

Lys Gln Lys Met Ala Glu Thr Lys Asp Lys Ala Lys Glu Lys Phe Phe
545                 550                 555                 560

Glu Ala Lys Asp Ala Thr Ala Asp Lys Leu Gly Asn Ala Lys Asp Ala
                565                 570                 575

Thr Lys Asp Lys Leu Gly Tyr Ala Ala Asp Lys Thr Lys Glu Lys Tyr
            580                 585                 590

Asp Glu Ala Lys Asp Ala Thr Lys Asp Lys Leu Gly Tyr Ala Lys Asp
        595                 600                 605

Lys Leu Val Glu Thr Lys Asp Ala Ala Lys Asp Lys Thr Lys Glu Lys
    610                 615                 620

Tyr Glu Glu Ala Lys Asp Lys Phe Gly Gln Ala Arg Asp Val Thr Lys
625                 630                 635                 640

Glu Arg Trp Asp Glu Thr Lys Asp Ala Ala Lys Asn Lys Tyr Gly Asp
                645                 650                 655

Met Arg Ser Asn Val Gln Met Glu Asn Trp Asn Asn Thr Arg Asp Arg
            660                 665                 670

Tyr Gly Asn Val Ile Gln Arg Pro Asp Glu Pro Arg Asp Lys Ile Thr
        675                 680                 685

Val Ala Ala Val Thr Thr Arg Glu Thr Val Thr Gln Ile Arg Lys Asp
    690                 695                 700

Asn Glu Pro Gln Thr Ile Ile Asn Asp Asn Pro Gln Lys Ala Arg Tyr
705                 710                 715                 720

Phe Glu Gln Tyr Ser Ala Val Tyr Val Asn Pro Gln Asp Gln Gln Lys
                725                 730                 735

Met Asp Lys Ile Ile Cys
            740

<210> SEQ ID NO 3
<211> LENGTH: 760
<212> TYPE: DNA
<213> ORGANISM: Polypedilum vanderplanki
<220> FEATURE:
<221> NAME/KEY: CDS
<222> LOCATION: (113)..(652)
<223> OTHER INFORMATION:

<400> SEQUENCE: 3
cctcgtgccg aacagtcata ttcagttcat caaacagtga agatataaaa aaatcagata      60 acaatttct  tctatttaac ttattacatt atcagaagat taagaaataa ca atg aaa    118
                                                         Met Lys
                                                           1 cac gac aag gga att atc gaa gaa gcc aaa gaa aaa atc atc gac gtt      166
His Asp Lys Gly Ile Ile Glu Glu Ala Lys Glu Lys Ile Ile Asp Val
      5                  10                  15
```

```
aaa gat gca gca aaa gaa aaa gtt caa aat gca gca gaa aca gta aag      214
Lys Asp Ala Ala Lys Glu Lys Val Gln Asn Ala Ala Glu Thr Val Lys
     20                  25                  30 aag gct ctt act ggt aat gag cat gaa atg gac gaa gct aag caa aca      262
Lys Ala Leu Thr Gly Asn Glu His Glu Met Asp Glu Ala Lys Gln Thr
 35                  40                  45                  50 atc aaa gat aaa gct tat gaa aca aaa gaa gct gtc aaa gat aaa gca      310
Ile Lys Asp Lys Ala Tyr Glu Thr Lys Glu Ala Val Lys Asp Lys Ala
                 55                  60                  65 cat gaa aca aaa gaa gca atc aaa gat aaa gca tat gat gca aaa gaa      358
His Glu Thr Lys Glu Ala Ile Lys Asp Lys Ala Tyr Asp Ala Lys Glu
             70                  75                  80 act gta aag gaa aag tat gaa aat gca aaa gag aaa gta aaa gat gct      406
Thr Val Lys Glu Lys Tyr Glu Asn Ala Lys Glu Lys Val Lys Asp Ala
         85                  90                  95 ggt gat gga att aaa gat aag tat gat gca acc aaa gaa gct gca aga      454
Gly Asp Gly Ile Lys Asp Lys Tyr Asp Ala Thr Lys Glu Ala Ala Arg
    100                 105                 110 gac act tat gaa gat gca aag aaa aaa gtt aaa gga act gat gaa gaa      502
Asp Thr Tyr Glu Asp Ala Lys Lys Lys Val Lys Gly Thr Asp Glu Glu
115                 120                 125                 130 tgg aag cca atg gag aca aaa gaa gaa tat ctc aaa gat aaa tat tac      550
Trp Lys Pro Met Glu Thr Lys Glu Glu Tyr Leu Lys Asp Lys Tyr Tyr
                135                 140                 145 aaa aac aat ttc aat cca att gcc atc ttc gaa tca atc atg caa cca      598
Lys Asn Asn Phe Asn Pro Ile Ala Ile Phe Glu Ser Ile Met Gln Pro
            150                 155                 160 gaa tca tca caa atg gct tca ttg gct ttg aac act ttg cga cga att      646
Glu Ser Ser Gln Met Ala Ser Leu Ala Leu Asn Thr Leu Arg Arg Ile
        165                 170                 175 cca aaa taaacacagt acttaaaatt attgtagaaa aattaatgaa tggaaaagat      702
Pro Lys
    180 ttgaataaaa ttagaatatc agagctttta aagactgcaa aaaaaaaaa aaaaaaa      760

<210> SEQ ID NO 4
<211> LENGTH: 180
<212> TYPE: PRT
<213> ORGANISM: Polypedilum vanderplanki

<400> SEQUENCE: 4

Met Lys His Asp Lys Gly Ile Ile Glu Glu Ala Lys Glu Lys Ile Ile
1               5                   10                  15

Asp Val Lys Asp Ala Ala Lys Glu Lys Val Gln Asn Ala Ala Glu Thr
            20                  25                  30

Val Lys Lys Ala Leu Thr Gly Asn Glu His Glu Met Asp Glu Ala Lys
        35                  40                  45

Gln Thr Ile Lys Asp Lys Ala Tyr Glu Thr Lys Glu Ala Val Lys Asp
    50                  55                  60

Lys Ala His Glu Thr Lys Glu Ala Ile Lys Asp Lys Ala Tyr Asp Ala
65                  70                  75                  80

Lys Glu Thr Val Lys Glu Lys Tyr Glu Asn Ala Lys Glu Lys Val Lys
                85                  90                  95

Asp Ala Gly Asp Gly Ile Lys Asp Lys Tyr Asp Ala Thr Lys Glu Ala
            100                 105                 110

Ala Arg Asp Thr Tyr Glu Asp Ala Lys Lys Lys Val Lys Gly Thr Asp
        115                 120                 125

Glu Glu Trp Lys Pro Met Glu Thr Lys Glu Glu Tyr Leu Lys Asp Lys
    130                 135                 140
```

```
Tyr Tyr Lys Asn Asn Phe Asn Pro Ile Ala Ile Phe Glu Ser Ile Met
145                 150                 155                 160

Gln Pro Glu Ser Ser Gln Met Ala Ser Leu Ala Leu Asn Thr Leu Arg
            165                 170                 175

Arg Ile Pro Lys
            180

<210> SEQ ID NO 5
<211> LENGTH: 1591
<212> TYPE: DNA
<213> ORGANISM: Polypedilum vanderplanki
<220> FEATURE:
<221> NAME/KEY: CDS
<222> LOCATION: (19)..(1470)
<223> OTHER INFORMATION:

<400> SEQUENCE: 5
agtcttaatt cattcatc atg gag aaa aca tta aac gag aaa acg att tta         51
                    Met Glu Lys Thr Leu Asn Glu Lys Thr Ile Leu
                      1               5                  10 caa cca aaa act gtc ttt aat att gac aat ttc ctc ggt ctc ttt tct         99
Gln Pro Lys Thr Val Phe Asn Ile Asp Asn Phe Leu Gly Leu Phe Ser
             15                  20                  25 tta gaa gct gga gga att ttt att gga tct gtc ggt tta gtt tgg tcg        147
Leu Glu Ala Gly Gly Ile Phe Ile Gly Ser Val Gly Leu Val Trp Ser
         30                  35                  40 ata gtc caa gta ttt cta cat tcg gca tct tta tta tct atg aaa tat        195
Ile Val Gln Val Phe Leu His Ser Ala Ser Leu Leu Ser Met Lys Tyr
     45                  50                  55 gtc gac aac ttc tgc cca caa tgg cca aag att ttc cat tat ctt aca        243
Val Asp Asn Phe Cys Pro Gln Trp Pro Lys Ile Phe His Tyr Leu Thr
 60                  65                  70                  75 cga ttt cca caa caa gct cat cag gga ata aaa aat gtt aca aat atg        291
Arg Phe Pro Gln Gln Ala His Gln Gly Ile Lys Asn Val Thr Asn Met
                 80                  85                  90 gca agt gaa ggc tat gaa gtt cta aag aac aaa att ccg gaa ggw tat        339
Ala Ser Glu Gly Tyr Glu Val Leu Lys Asn Lys Ile Pro Glu Xaa Tyr
             95                 100                 105 gaa gya cta aar gac aaa ctt cca gat ggc tac gaa gca tta aag gac        387
Glu Xaa Leu Lys Asp Lys Leu Pro Asp Gly Tyr Glu Ala Leu Lys Asp
        110                 115                 120 aaa att cct gaa acc tac gag act tta aaa aac aaa att cca gaa ggc        435
Lys Ile Pro Glu Thr Tyr Glu Thr Leu Lys Asn Lys Ile Pro Glu Gly
    125                 130                 135 tac gaa gct tta aaa gat aaa att cca gat ggt ata aaa gaa gct gca        483
Tyr Glu Ala Leu Lys Asp Lys Ile Pro Asp Gly Ile Lys Glu Ala Ala
140                 145                 150                 155 caa act gct cag gaa act ttt atg gat act tct gga aga gtt caa gaa        531
Gln Thr Ala Gln Glu Thr Phe Met Asp Thr Ser Gly Arg Val Gln Glu
                160                 165                 170 ggc ata aaa gag gct gca gta aaa att aag gaa ggt gtt aga gat gcc        579
Gly Ile Lys Glu Ala Ala Val Lys Ile Lys Glu Gly Val Arg Asp Ala
            175                 180                 185 tca gga aga gta caa gaa aat tta caa gat gta act gga aaa gtt caa        627
Ser Gly Arg Val Gln Glu Asn Leu Gln Asp Val Thr Gly Lys Val Gln
        190                 195                 200 gac aaa ttt aac gac gta tca gga agt ata aag gat aat yta cca aat        675
Asp Lys Phe Asn Asp Val Ser Gly Ser Ile Lys Asp Asn Xaa Pro Asn
    205                 210                 215 gtt gca gga aga gtt cag gac aaa ttt aat gac gta tca gga gct ata        723
Val Ala Gly Arg Val Gln Asp Lys Phe Asn Asp Val Ser Gly Ala Ile
```

|  |  |  |  |  |  |  |  |  |  |  |  |  |  |  |  |
|---|---|---|---|---|---|---|---|---|---|---|---|---|---|---|---|
|  |  | 220 |  |  | 225 |  |  | 230 |  |  | 235 |  |  |  |  |

```
aaa gat aat cta cca gac gtt gca gga aga gtc aaa gac aat tta tct        771
Lys Asp Asn Leu Pro Asp Val Ala Gly Arg Val Lys Asp Asn Leu Ser
                240                 245                 250 gaa gta act gga aaa gtt cag gat aag ttt aac gac gta tca gga agt        819
Glu Val Thr Gly Lys Val Gln Asp Lys Phe Asn Asp Val Ser Gly Ser
        255                 260                 265 ata aaa gat aat tta cca aat gtt gct ggg aaa gtt caa gaa ggt tac        867
Ile Lys Asp Asn Leu Pro Asn Val Ala Gly Lys Val Gln Glu Gly Tyr
    270                 275                 280 gaa aac atc aaa aat cgt gca cca gaa act ttc cat gat gca aaa aat        915
Glu Asn Ile Lys Asn Arg Ala Pro Glu Thr Phe His Asp Ala Lys Asn
285                 290                 295 cga ctc ggr gat tca tac gat gaw att aag aga cgt gtt ggt gaa aaa        963
Arg Leu Xaa Asp Ser Tyr Asp Xaa Ile Lys Arg Arg Val Gly Glu Lys
300                 305                 310                 315 tat tac gac gta aaa gac caa gct caa gga aca ttt tac gat gtt aaa       1011
Tyr Tyr Asp Val Lys Asp Gln Ala Gln Gly Thr Phe Tyr Asp Val Lys
                320                 325                 330 aat aaa gca gga gaa aaa tta caa gat gtw gca aat gaa gaa act tgc       1059
Asn Lys Ala Gly Glu Lys Leu Gln Asp Xaa Ala Asn Glu Glu Thr Cys
        335                 340                 345 tca gaa atc agc aag tat tct ttt ggt gca ttg atg ttg ttt ttg att       1107
Ser Glu Ile Ser Lys Tyr Ser Phe Gly Ala Leu Met Leu Phe Leu Ile
    350                 355                 360 ggg gca aac att gtt tcg att gtc gct cac tac aga ttg atc aaa gca       1155
Gly Ala Asn Ile Val Ser Ile Val Ala His Tyr Arg Leu Ile Lys Ala
365                 370                 375 gtt gag gag tcc aat gca tca aaa ttg cga ttg tca ctt tgc tac tac       1203
Val Glu Glu Ser Asn Ala Ser Lys Leu Arg Leu Ser Leu Cys Tyr Tyr
380                 385                 390                 395 aaa ttt ttc atc ggt ttc aag ctt gtc ttc ttg gcc att ctt gga gtt       1251
Lys Phe Phe Ile Gly Phe Lys Leu Val Phe Leu Ala Ile Leu Gly Val
                400                 405                 410 tca tca ctt tac tca gaa gag atg ttt tat cca gcg atc tca ctt ttg       1299
Ser Ser Leu Tyr Ser Glu Glu Met Phe Tyr Pro Ala Ile Ser Leu Leu
        415                 420                 425 gtt ctt ctt ttg atc gac att tat att ttc aat gtc ctt gac acg ctc       1347
Val Leu Leu Leu Ile Asp Ile Tyr Ile Phe Asn Val Leu Asp Thr Leu
    430                 435                 440 tct ttt gtg ttt tca aac act cca cat aaa act gtt ttg tac aca caa       1395
Ser Phe Val Phe Ser Asn Thr Pro His Lys Thr Val Leu Tyr Thr Gln
445                 450                 455 caa atc ata aga aag aag gaa att tat gat gaa att cct cat aat gaa       1443
Gln Ile Ile Arg Lys Lys Glu Ile Tyr Asp Glu Ile Pro His Asn Glu
460                 465                 470                 475 gac ctc gaa atc gaa gat aaa tct aag taaaacgttc acctaaagta             1490
Asp Leu Glu Ile Glu Asp Lys Ser Lys
                480 agttttgta aaattttat tcttgcgttt ctctcttcat ataatgataa taaaatgtaa       1550
attttaaaaa acaaaaaaaa aaaaaaaaaa aaaaaaaaa a                          1591

<210> SEQ ID NO 6
<211> LENGTH: 484
<212> TYPE: PRT
<213> ORGANISM: Polypedilum vanderplanki
<220> FEATURE:
<221> NAME/KEY: misc_feature
<222> LOCATION: (106)..(106)
<223> OTHER INFORMATION: The 'Xaa' at location 106 stands for Gly.
<220> FEATURE:
```

```
<221> NAME/KEY: misc_feature
<222> LOCATION: (109)..(109)
<223> OTHER INFORMATION: The 'Xaa' at location 109 stands for Ala, or
      Val.
<220> FEATURE:
<221> NAME/KEY: misc_feature
<222> LOCATION: (217)..(217)
<223> OTHER INFORMATION: The 'Xaa' at location 217 stands for Leu.
<220> FEATURE:
<221> NAME/KEY: misc_feature
<222> LOCATION: (302)..(302)
<223> OTHER INFORMATION: The 'Xaa' at location 302 stands for Gly.
<220> FEATURE:
<221> NAME/KEY: misc_feature
<222> LOCATION: (307)..(307)
<223> OTHER INFORMATION: The 'Xaa' at location 307 stands for Glu, or
      Asp.
<220> FEATURE:
<221> NAME/KEY: misc_feature
<222> LOCATION: (341)..(341)
<223> OTHER INFORMATION: The 'Xaa' at location 341 stands for Val.

<400> SEQUENCE: 6

Met Glu Lys Thr Leu Asn Glu Lys Thr Ile Leu Gln Pro Lys Thr Val
1               5                   10                  15

Phe Asn Ile Asp Asn Phe Leu Gly Leu Phe Ser Leu Glu Ala Gly Gly
            20                  25                  30

Ile Phe Ile Gly Ser Val Gly Leu Val Trp Ser Ile Val Gln Val Phe
        35                  40                  45

Leu His Ser Ala Ser Leu Leu Ser Met Lys Tyr Val Asp Asn Phe Cys
    50                  55                  60

Pro Gln Trp Pro Lys Ile Phe His Tyr Leu Thr Arg Phe Pro Gln Gln
65                  70                  75                  80

Ala His Gln Gly Ile Lys Asn Val Thr Asn Met Ala Ser Glu Gly Tyr
                85                  90                  95

Glu Val Leu Lys Asn Lys Ile Pro Glu Xaa Tyr Glu Xaa Leu Lys Asp
            100                 105                 110

Lys Leu Pro Asp Gly Tyr Glu Ala Leu Lys Asp Lys Ile Pro Glu Thr
        115                 120                 125

Tyr Glu Thr Leu Lys Asn Lys Ile Pro Glu Gly Tyr Glu Ala Leu Lys
    130                 135                 140

Asp Lys Ile Pro Asp Gly Ile Lys Glu Ala Ala Gln Thr Ala Gln Glu
145                 150                 155                 160

Thr Phe Met Asp Thr Ser Gly Arg Val Gln Glu Gly Ile Lys Glu Ala
                165                 170                 175

Ala Val Lys Ile Lys Glu Gly Val Arg Asp Ala Ser Gly Arg Val Gln
            180                 185                 190

Glu Asn Leu Gln Asp Val Thr Gly Lys Val Gln Asp Lys Phe Asn Asp
        195                 200                 205

Val Ser Gly Ser Ile Lys Asp Asn Xaa Pro Asn Val Ala Gly Arg Val
    210                 215                 220

Gln Asp Lys Phe Asn Asp Val Ser Gly Ala Ile Lys Asp Asn Leu Pro
225                 230                 235                 240

Asp Val Ala Gly Arg Val Lys Asp Asn Leu Ser Glu Val Thr Gly Lys
                245                 250                 255

Val Gln Asp Lys Phe Asn Asp Val Ser Gly Ser Ile Lys Asp Asn Leu
            260                 265                 270

Pro Asn Val Ala Gly Lys Val Gln Glu Gly Tyr Glu Asn Ile Lys Asn
        275                 280                 285

Arg Ala Pro Glu Thr Phe His Asp Ala Lys Asn Arg Leu Xaa Asp Ser
    290                 295                 300
```

```
Tyr Asp Xaa Ile Lys Arg Arg Val Gly Glu Lys Tyr Tyr Asp Val Lys
305                 310                 315                 320

Asp Gln Ala Gln Gly Thr Phe Tyr Asp Val Lys Asn Lys Ala Gly Glu
            325                 330                 335

Lys Leu Gln Asp Xaa Ala Asn Glu Glu Thr Cys Ser Glu Ile Ser Lys
            340                 345                 350

Tyr Ser Phe Gly Ala Leu Met Leu Phe Leu Ile Gly Ala Asn Ile Val
            355                 360                 365

Ser Ile Val Ala His Tyr Arg Leu Ile Lys Ala Val Glu Glu Ser Asn
370                 375                 380

Ala Ser Lys Leu Arg Leu Ser Leu Cys Tyr Tyr Lys Phe Phe Ile Gly
385                 390                 395                 400

Phe Lys Leu Val Phe Leu Ala Ile Leu Gly Val Ser Ser Leu Tyr Ser
                405                 410                 415

Glu Glu Met Phe Tyr Pro Ala Ile Ser Leu Leu Val Leu Leu Leu Ile
            420                 425                 430

Asp Ile Tyr Ile Phe Asn Val Leu Asp Thr Leu Ser Phe Val Phe Ser
            435                 440                 445

Asn Thr Pro His Lys Thr Val Leu Tyr Thr Gln Gln Ile Ile Arg Lys
450                 455                 460

Lys Glu Ile Tyr Asp Glu Ile Pro His Asn Glu Asp Leu Glu Ile Glu
465                 470                 475                 480

Asp Lys Ser Lys

<210> SEQ ID NO 7
<211> LENGTH: 143
<212> TYPE: PRT
<213> ORGANISM: Aphelenchus avenae

<400> SEQUENCE: 7

Met Ser Ser Gln Gln Asn Gln Asn Arg Gln Gly Glu Gln Gln Glu Gln
1               5                   10                  15

Gly Tyr Met Glu Ala Ala Lys Glu Lys Val Val Asn Ala Trp Glu Ser
            20                  25                  30

Thr Lys Glu Thr Leu Ser Ser Thr Ala Gln Ala Ala Glu Lys Thr
        35                  40                  45

Ala Glu Phe Arg Asp Ser Ala Gly Glu Thr Ile Arg Asp Leu Thr Gly
50                  55                  60

Gln Ala Gln Glu Lys Gly Gln Glu Phe Lys Glu Arg Ala Gly Glu Lys
65                  70                  75                  80

Ala Glu Glu Thr Lys Gln Arg Ala Gly Glu Lys Met Asp Glu Thr Lys
                85                  90                  95

Gln Arg Ala Gly Glu Met Arg Glu Asn Ala Gly Gln Lys Met Glu Glu
            100                 105                 110

Tyr Lys Gln Gln Gly Lys Gly Lys Ala Glu Glu Leu Arg Asp Thr Ala
            115                 120                 125

Ala Glu Lys Leu His Gln Ala Gly Glu Lys Val Lys Gly Arg Asp
130                 135                 140

<210> SEQ ID NO 8
<211> LENGTH: 474
<212> TYPE: PRT
<213> ORGANISM: Betula pendula

<400> SEQUENCE: 8

Met Ala Ser Ser Arg Glu Phe Lys Glu Lys Arg Ala Glu Ala Ala Ala
```

```
1               5                   10                  15
Lys Leu Ala Ala Ser Asp Leu Glu Asp Val Lys Arg Glu Arg Glu Tyr
                20                  25                  30
Glu Glu Gln Ala Lys Met Glu Arg Glu Leu Ser Leu Gln Gln Gln
            35                  40                  45
Gln Glu Asp Arg Pro Gly Val Ile Gly Ser Val Leu Lys Ala Val His
        50                  55                  60
Glu Thr Tyr Glu His Ala Lys Glu Ala Val Val Gly Lys Thr Glu Glu
65                  70                  75                  80
Thr Ala Glu Ser Thr Arg Glu Ser Gly Glu Asn Ala Ala Glu Lys Ala
                85                  90                  95
Arg Lys Thr Lys Asp Ser Ala Ala Glu Lys Thr Arg Glu Thr Lys Lys
                100                 105                 110
Cys Ala Ala Glu Lys Ala Lys Glu Tyr Lys Asp Tyr Thr Ala Glu Lys
                115                 120                 125
Ala Arg Glu Thr Thr Glu Lys Ala Arg Glu Thr Lys Asp Ser Ala Ala
            130                 135                 140
Glu Lys Ala Arg Glu Thr Lys Asp Ser Ala Ala Glu Lys Ala Lys Glu
145                 150                 155                 160
Tyr Lys Asp Tyr Thr Ala Glu Lys Thr Arg Glu Thr Arg Glu Ser Ala
                165                 170                 175
Lys Glu Lys Ala Lys Glu Ala Ala Glu Lys Ala Lys Glu Thr Lys Asp
                180                 185                 190
Ser Ala Leu Gly Lys Ala Glu Glu Tyr Lys Asp Tyr Ala Ala Glu Lys
            195                 200                 205
Ala Lys Glu Ala Lys Asp Lys Thr Val Gly Lys Ala Ser Glu Tyr Lys
        210                 215                 220
Asp Tyr Ala Ala Glu Lys Ala Lys Glu Thr Lys Asp Ser Ala Leu Gly
225                 230                 235                 240
Lys Ala Glu Glu Tyr Lys Asp Tyr Thr Ala Lys Glu Lys Glu Val
                245                 250                 255
Lys Asp Lys Thr Val Gly Lys Ala Gly Glu Tyr Lys Asp Tyr Ala Ala
            260                 265                 270
Glu Lys Ala Lys Glu Thr Lys Asp Tyr Thr Ala Glu Lys Thr Ile Glu
        275                 280                 285
Gly Lys Asp Thr Thr Leu Ser Lys Leu Gly Glu Leu Lys Glu Ser Ala
        290                 295                 300
Ala Asp Ala Ala Arg Arg Ala Met Gly Phe Leu Ser Gly Lys Lys Asp
305                 310                 315                 320
Glu Val Thr Gln Lys Thr Glu Glu Thr Lys Glu Ala Thr Lys Glu Lys
                325                 330                 335
Leu Ser Glu Ala Glu Glu Ala Arg Arg Lys Met Glu Glu Leu Lys
            340                 345                 350
Val Arg Gly Glu Glu Asn Lys Asp Asp Ala Asp Arg Lys Asp Arg Glu
        355                 360                 365
Asp Asn Lys Val Asn Glu Ala Asp Arg Gly Thr Ala Ala Thr Ala Asn
        370                 375                 380
Ile Phe Ser Ser Leu Pro Ser Val Thr Glu Ala Ile Lys Arg Lys Leu
385                 390                 395                 400
Thr Gln Pro Ser Asp Val Val Asp Glu Thr Arg Ala Ala Arg Glu His
            405                 410                 415
Gly Ser Thr Gly Arg Lys Glu Ala Gly Lys Val Val Asp Val Glu
            420                 425                 430
```

Glu Thr Arg Pro Gly Tyr Ile Ala Ala Lys Leu Lys Glu Ser Asp Gln
    435                 440                 445

Met Ala Gly Gln Thr Phe Asn Asp Pro Gly Arg Arg Asp Asp Glu Gly
    450                 455                 460

Gly Ile Arg Leu Asp Arg Gln Gly Lys Met
465                 470

<210> SEQ ID NO 9
<211> LENGTH: 463
<212> TYPE: PRT
<213> ORGANISM: Glycine max

<400> SEQUENCE: 9

Met Ala Ser Lys Lys Gln Glu Glu Arg Ala Glu Ala Ala Lys Val
1               5                   10                  15

Ala Ala Lys Glu Leu Glu Gln Val Asn Arg Glu Arg Asp Arg Asp
                20                  25                  30

Phe Gly Val Val Ala Glu Gln Gln Gln His His Gln Glu Asp Gln
                35                  40                  45

Gln Lys Arg Gly Val Ile Gly Ser Met Phe Lys Ala Val Gln Asp Thr
    50                  55                  60

Tyr Glu Asn Ala Lys Glu Ala Val Val Gly Lys Lys Glu Ala Thr Asn
65                  70                  75                  80

Asn Ala Tyr Ser Asn Thr Glu Val Ile His Asp Val Asn Ile Gln Pro
                85                  90                  95

Asp Asp Val Ser Ala Thr Gly Glu Val Arg Asp Ile Ser Ala Thr Lys
                100                 105                 110

Thr His Asp Ile Tyr Asp Ser Ala Thr Asp Asn Asn Asn Lys Thr
        115                 120                 125

Gly Ser Lys Val Gly Glu Tyr Ala Asp Tyr Ala Ser Gln Lys Ala Lys
    130                 135                 140

Glu Thr Lys Asp Ala Thr Met Glu Lys Ala Gly Glu Tyr Thr Asp Tyr
145                 150                 155                 160

Ala Ser Gln Lys Ala Lys Glu Ala Lys Lys Thr Thr Met Glu Lys Gly
                165                 170                 175

Gly Glu Tyr Lys Asp Tyr Ser Ala Glu Lys Ala Lys Glu Arg Lys Asp
                180                 185                 190

Ala Thr Val Asn Lys Met Gly Glu Tyr Lys Asp Tyr Ala Ala Glu Lys
                195                 200                 205

Ala Lys Glu Gly Lys Asp Ala Thr Val Asn Lys Met Gly Glu Tyr Lys
    210                 215                 220

Asp Tyr Ala Ala Glu Lys Thr Lys Glu Gly Lys Asp Ala Thr Val Asn
225                 230                 235                 240

Lys Met Gly Glu Tyr Lys Asp Tyr Thr Ala Glu Lys Ala Lys Glu Gly
                245                 250                 255

Lys Asp Thr Thr Leu Gly Lys Leu Gly Glu Leu Lys Asp Thr Ala Ser
                260                 265                 270

Asp Ala Ala Lys Arg Ala Val Gly Tyr Leu Ser Gly Lys Lys Glu Glu
    275                 280                 285

Thr Lys Glu Met Ala Ser Glu Thr Ala Glu Ala Thr Ala Asn Lys Ala
    290                 295                 300

Gly Glu Met Lys Glu Ala Thr Lys Lys Thr Ala Glu Thr Ala Glu
305                 310                 315                 320

Ala Ala Lys Asn Lys Ala Gly Glu Ile Lys Asp Arg Ala Ala Glu Thr
                325                 330                 335

Ala Glu Ala Ala Lys Asn Lys Thr Ala Glu Thr Ala Glu Val Thr Lys
    340                 345                 350

Asn Lys Ala Leu Glu Met Lys Asp Ala Ala Lys Asp Arg Thr Ala Glu
            355                 360                 365

Thr Thr Asp Ala Ala Lys Gln Lys Thr Ala Gln Ala Lys Glu Asn Thr
    370                 375                 380

Lys Glu Asn Val Ser Gly Ala Gly Glu Thr Ala Arg Arg Lys Met Glu
385                 390                 395                 400

Glu Pro Lys Leu Gln Gly Lys Glu Gly Tyr Gly Arg Gly Asp Lys
            405                 410                 415

Val Val Val Lys Val Glu Glu Ser Arg Pro Gly Ala Ile Ala Glu Thr
            420                 425                 430

Leu Lys Ala Ala Asp Gln Ile Ala Gly Gln Thr Phe Asn Asp Val Gly
            435                 440                 445

Arg Phe Asp Glu Glu Gly Val Val Asn Val Glu Arg Lys Lys
    450                 455                 460

<210> SEQ ID NO 10
<211> LENGTH: 221
<212> TYPE: PRT
<213> ORGANISM: Zea mays

<400> SEQUENCE: 10

Met Ala Ser His Gln Asp Lys Ala Ser Tyr Gln Ala Gly Glu Thr Lys
1               5                   10                  15

Ala Arg Thr Glu Glu Lys Thr Gly Gln Ala Val Gly Ala Thr Lys Asp
            20                  25                  30

Thr Ala Gln His Ala Lys Asp Arg Ala Ala Asp Ala Ala Gly His Ala
        35                  40                  45

Ala Gly Lys Gly Gln Asp Ala Lys Glu Ala Thr Lys Gln Lys Ala Ser
    50                  55                  60

Asp Thr Gly Ser Tyr Leu Gly Lys Thr Asp Glu Ala Lys His Lys
65                  70                  75                  80

Ala Gly Glu Thr Thr Glu Ala Thr Lys His Lys Ala Gly Glu Thr Thr
                85                  90                  95

Glu Ala Ala Lys Gln Lys Ala Gly Glu Thr Thr Glu Ala Ala Lys Gln
            100                 105                 110

Lys Ala Gly Glu Thr Thr Glu Thr Thr Lys Gln Lys Ala Gly Glu Thr
        115                 120                 125

Thr Glu Ala Ala Arg Gln Lys Ala Ala Asp Ala Met Glu Ala Ala Lys
    130                 135                 140

Gln Lys Ala Ala Glu Ala Gly Gln Tyr Ala Lys Asp Thr Ala Val Ser
145                 150                 155                 160

Gly Lys Asp Lys Ser Gly Gly Val Ile Gln Gln Ala Thr Glu Gln Val
                165                 170                 175

Lys Ser Ala Ala Ala Gly Arg Lys Asp Ala Val Met Ser Thr Leu Gly
            180                 185                 190

Met Gly Gly Asp Asn Lys Gln Gly Asp Ala Asn Thr Asn Thr Asn Thr
        195                 200                 205

Asn Thr Thr Lys Asp Ser Ser Thr Ile Thr Arg Asp His
    210                 215                 220

<210> SEQ ID NO 11
<211> LENGTH: 480
<212> TYPE: PRT
<213> ORGANISM: Arabidopsis thaliana

<400> SEQUENCE: 11

```
Met Thr Asn Leu Leu Ala Leu Cys Leu Val Leu Ser Thr Leu Leu Ala
1               5                   10                  15

Ala Glu Val Trp Ser Pro Ser Pro Ala Met Thr Thr His Asn Thr Ala
            20                  25                  30

Val Ala Ser Glu Gly Glu Val Ile Val Lys Asp Gly His His Val Val
        35                  40                  45

Val Val Glu Tyr Asp Arg Asp Gly Lys Thr Asn Thr Arg Val Ser Ile
    50                  55                  60

Ser Pro Pro Ser Ala Asp Gln Gly Glu Lys Glu Asn Glu Val Glu
65                  70                  75                  80

Met Gly Thr Ser Met Phe Arg Asn Val Lys Glu Lys Ala Lys Glu Thr
                85                  90                  95

Ala Ser Tyr Leu Pro His Val Gly Gln Gly Ile Ser Gln Pro Val Met
            100                 105                 110

Thr Asp Glu Ala Arg Asp His His Ala Thr Ala Gly Val Ile Cys
        115                 120                 125

Asp Ala Phe Gly Lys Cys Arg Gln Lys Ile Ala Ser Val Val Gly Arg
    130                 135                 140

Ala Lys Asp Arg Thr Val Asp Ser Val Gly Glu Thr Ala Ser Asp Val
145                 150                 155                 160

Arg Glu Ala Ala Ala His Lys Ala His Asp Val Lys Glu Thr Val Thr
                165                 170                 175

His Ala Ala Arg Asp Val Glu Asp Thr Val Ala Asp Gln Ala Gln Tyr
            180                 185                 190

Ala Lys Gly Arg Val Thr Glu Lys Ala His Asp Pro Lys Glu Gly Val
        195                 200                 205

Ala His Lys Ala His Asp Ala Lys Glu Ser Val Ala Asp Lys Ala His
    210                 215                 220

Asp Ala Lys Glu Ser Val Ala Gln Lys Ala His Asp Ala Lys Glu Lys
225                 230                 235                 240

Val Arg Glu Lys Ala His Asp Val Lys Glu Thr Val Ala Gln Lys Ala
                245                 250                 255

His Glu Ser Lys Glu Arg Ala Lys Asp Arg Val Arg Glu Lys Ala Gln
            260                 265                 270

Glu Leu Lys Glu Thr Ala Thr His Lys Ser Lys Asn Ala Trp Glu Arg
        275                 280                 285

Val Lys Asn Gly Ala Arg Glu Phe Gly Ser Ala Thr Ala Ala Thr Leu
    290                 295                 300

Ser Pro Thr Lys Val Ala Ser Ile Val Gly Leu Thr Gly Ile Ala Ala
305                 310                 315                 320

Ala Phe Gly Thr Ser Val Trp Val Thr Phe Val Ser Ser Tyr Val Leu
                325                 330                 335

Ala Ser Val Leu Gly Arg Gln Gln Phe Gly Val Val Gln Ser Lys Leu
            340                 345                 350

Tyr Pro Val Tyr Phe Lys Ala Thr Ser Val Gly Ile Leu Val Gly Leu
        355                 360                 365

Phe Gly His Val Leu Ser Arg Arg Lys Leu Leu Thr Asp Ala Thr
    370                 375                 380

Glu Met Trp Gln Gly Val Asn Leu Leu Ser Ser Phe Phe Met Ile Glu
385                 390                 395                 400

Ala Asn Lys Ser Phe Val Glu Pro Arg Ala Thr Lys Ala Met Phe Glu
                405                 410                 415
```

```
Arg Met Lys Ala Glu Lys Glu Gly Arg Gly Gly Glu Arg Thr Ser
            420                 425                 430

Glu Gln Glu Leu Arg Arg Lys Leu Glu Gln Leu Ser Glu Arg Leu Ser
        435                 440                 445

Lys Leu Asn Thr Tyr Ser Ser Trp Leu Asn Ile Leu Thr Leu Met Ser
    450                 455                 460

Leu Thr Trp His Phe Val Tyr Leu Gly Gln Arg Leu Gly Ala Ala Cys
465             470                 475                 480

<210> SEQ ID NO 12
<211> LENGTH: 39
<212> TYPE: DNA
<213> ORGANISM: Artificial
<220> FEATURE:
<223> OTHER INFORMATION: An artificially synthesized primer sequence

<400> SEQUENCE: 12
gcgtaatacg actcactata gggaacaaaa gctggagct                              39
```